(12) United States Patent
Amarasingham et al.

(10) Patent No.: US 10,496,788 B2
(45) Date of Patent: Dec. 3, 2019

(54) HOLISTIC HOSPITAL PATIENT CARE AND MANAGEMENT SYSTEM AND METHOD FOR AUTOMATED PATIENT MONITORING

(71) Applicant: Parkland Center for Clinical Innovation, Dallas, TX (US)

(72) Inventors: Rubendran Amarasingham, Dallas, TX (US); George R. Oliver, Southlake, TX (US); Anand R. Shah, Dallas, TX (US); Vaidyanatha Siva, Plano, TX (US); Brian O. Lucena, Dallas, TX (US); Monal Shah, Dallas, TX (US); Praseetha Cherian, Irving, TX (US); Spencer Ballard, Allen, TX (US); Jason McGinn, Keller, TX (US)

(73) Assignee: Parkland Center for Clinical Innovation, Dallas, TX (US)

( * ) Notice: Subject to any disclaimer, the term of this patent is extended or adjusted under 35 U.S.C. 154(b) by 497 days.

(21) Appl. No.: 14/682,836

(22) Filed: Apr. 9, 2015

(65) Prior Publication Data
US 2015/0213224 A1    Jul. 30, 2015

Related U.S. Application Data

(63) Continuation-in-part of application No. 13/613,980, filed on Sep. 13, 2012, now Pat. No. 9,536,052.
(Continued)

(51) Int. Cl.
*G06N 5/02* (2006.01)
*G06F 19/00* (2018.01)
(Continued)

(52) U.S. Cl.
CPC ............. *G06F 19/00* (2013.01); *G16H 50/30* (2018.01); *G16H 50/50* (2018.01); *G06N 5/02* (2013.01);
(Continued)

(58) Field of Classification Search
None
See application file for complete search history.

(56) References Cited

U.S. PATENT DOCUMENTS

| | | |
|---|---|---|
| 3,225,179 A | 12/1965 | Harold et al. |
| 5,583,758 A | 12/1996 | McIlroy et al. |
| (Continued) | | |

FOREIGN PATENT DOCUMENTS

| | | |
|---|---|---|
| WO | 2013033655 A1 | 3/2013 |
| WO | 2014042942 A1 | 3/2014 |
| WO | 2014105752 A1 | 7/2014 |

OTHER PUBLICATIONS

Liu, et al., Integration of RFID and Wireless Sensor Networks, University of Birmingham, 2008, pp. 1-29.*
(Continued)

*Primary Examiner* — Wilbert L Starks
(74) *Attorney, Agent, or Firm* — Wei Wei Jeang; Grable Martin Fulton PLLC

(57) ABSTRACT

A holistic hospital patient care and management system comprises a data store to receive and store patient data including clinical and non-clinical data; a plurality of RFID sensors to detect a plurality of RFID tags associated with patients to enable real-time tracking of location; at least one predictive model including a plurality of weighted risk variables and risk thresholds in consideration of the clinical and non-clinical data and configured to identify at least one medical condition associated with the patients; a risk logic module configured to apply at least one predictive model to the clinical and non-clinical data to determine at least one risk score associated with each patient; a patient monitoring logic module configured to receive location data of the patients and determine patient real-time location and status; and a user interface module configured to display patient
(Continued)

medical condition, risk score, location, and status information to authorized personnel.

20 Claims, 16 Drawing Sheets

Related U.S. Application Data

(60) Provisional application No. 61/978,058, filed on Apr. 10, 2014.

(51) Int. Cl.
*G16H 50/30* (2018.01)
*G16H 50/50* (2018.01)
G16H 10/60 (2018.01)
G16H 50/70 (2018.01)
G16H 50/20 (2018.01)

(52) U.S. Cl.
CPC ............. *G16H 10/60* (2018.01); *G16H 50/20* (2018.01); *G16H 50/70* (2018.01)

(56) References Cited

U.S. PATENT DOCUMENTS

| | | | |
|---|---|---|---|
| 5,950,214 A | 9/1999 | Rivette et al. | |
| 6,288,646 B1 | 9/2001 | Skardon | |
| 6,826,540 B1 | 11/2004 | Plantec et al. | |
| 7,395,216 B2 | 7/2008 | Rosenfeld et al. | |
| 7,490,085 B2 | 2/2009 | Walker et al. | |
| 7,617,078 B2 | 11/2009 | Rao et al. | |
| 8,077,042 B2 * | 12/2011 | Peeters ................ | A61B 5/0002 340/572.1 |
| 8,241,642 B2 | 8/2012 | Zagursky et al. | |
| 8,293,489 B2 | 10/2012 | Henkin | |
| 8,489,414 B2 | 7/2013 | McEachern | |
| 8,506,934 B2 | 8/2013 | Henkin | |
| 8,515,777 B1 | 8/2013 | Rajasenan | |
| 8,595,159 B2 | 11/2013 | McNair | |
| 8,663,938 B2 | 3/2014 | Henkin | |
| 8,682,696 B1 | 3/2014 | Shanmugam | |
| 8,859,004 B2 | 10/2014 | Zhang et al. | |
| 8,968,706 B2 | 3/2015 | Henkin | |
| 9,147,041 B2 | 9/2015 | Amarasingham et al. | |
| 2002/0116222 A1 | 8/2002 | Wurster | |
| 2002/0152096 A1 | 10/2002 | Falchuk et al. | |
| 2002/0169584 A1 | 11/2002 | Fu et al. | |
| 2003/0101076 A1 | 5/2003 | Zaleski | |
| 2004/0122706 A1 | 6/2004 | Walker et al. | |
| 2004/0122708 A1 | 6/2004 | Avinash et al. | |
| 2004/0242972 A1 | 12/2004 | Adak et al. | |
| 2005/0191716 A1 | 9/2005 | Surwit et al. | |
| 2005/0197982 A1 | 9/2005 | Saidi et al. | |
| 2005/0203773 A1 | 9/2005 | Soto et al. | |
| 2006/0031101 A1 | 2/2006 | Ross | |
| 2006/0036619 A1 | 2/2006 | Fuerst et al. | |
| 2006/0129427 A1 | 6/2006 | Wennberg | |
| 2006/0184489 A1 | 8/2006 | Weiner et al. | |
| 2006/0271408 A1 | 11/2006 | Rosenfeld et al. | |
| 2007/0021981 A1 | 1/2007 | Cox | |
| 2007/0073559 A1 | 3/2007 | Stangel | |
| 2007/0094048 A1 | 4/2007 | Grichnik | |
| 2007/0118399 A1 | 5/2007 | Avinash et al. | |
| 2007/0156456 A1 | 7/2007 | McGillin et al. | |
| 2007/0198296 A1 | 8/2007 | Pellinat et al. | |
| 2007/0255586 A1 | 11/2007 | Green et al. | |
| 2007/0288266 A1 | 12/2007 | Sysko et al. | |
| 2008/0010254 A1 | 1/2008 | Settimi | |
| 2008/0106374 A1 | 5/2008 | Sharbaugh | |
| 2008/0146277 A1 | 6/2008 | Anglin et al. | |
| 2008/0164998 A1 | 7/2008 | Scherpbier et al. | |
| 2008/0186137 A1 | 8/2008 | Butler et al. | |
| 2008/0235049 A1 | 9/2008 | Morita et al. | |
| 2008/0240425 A1 | 10/2008 | Rosales et al. | |

| | | |
|---|---|---|
| 2008/0275738 A1 | 11/2008 | Shillingburg |
| 2008/0306763 A1 | 12/2008 | James |
| 2009/0048866 A1 | 2/2009 | Mahesh et al. |
| 2009/0106692 A1 | 4/2009 | Bhavani |
| 2009/0164236 A1 | 6/2009 | Gounares et al. |
| 2009/0164248 A1 | 6/2009 | Hunt et al. |
| 2009/0240525 A1 | 9/2009 | Sadler et al. |
| 2009/0281838 A1 | 11/2009 | Lynn et al. |
| 2010/0001838 A1 | 1/2010 | Miodownik et al. |
| 2010/0017225 A1 | 1/2010 | Oakley et al. |
| 2010/0083164 A1 | 4/2010 | Martin et al. |
| 2010/0094648 A1 | 4/2010 | Seward |
| 2010/0114588 A1 | 5/2010 | Moitra et al. |
| 2010/0131434 A1 | 5/2010 | Magent et al. |
| 2010/0153270 A1 | 6/2010 | Hawkes |
| 2010/0177659 A1 | 7/2010 | Hethuin et al. |
| 2010/0189236 A1 | 7/2010 | MacDonald |
| 2010/0249531 A1 | 9/2010 | Hanlon et al. |
| 2010/0280847 A1 | 11/2010 | Schaffer |
| 2011/0009760 A1 | 1/2011 | Zhang et al. |
| 2011/0077973 A1 | 3/2011 | Breitenstein et al. |
| 2011/0093288 A1 | 4/2011 | Soto et al. |
| 2011/0099487 A1 | 4/2011 | Pyhalammi et al. |
| 2011/0145018 A1 | 6/2011 | Fotsch et al. |
| 2011/0145041 A1 | 6/2011 | Salamatov et al. |
| 2011/0184250 A1 | 7/2011 | Schmidt et al. |
| 2011/0202486 A1 | 8/2011 | Fung et al. |
| 2011/0218253 A1 | 9/2011 | Lange et al. |
| 2011/0225114 A1 | 9/2011 | Gotthardt |
| 2011/0295621 A1 | 12/2011 | Farooq et al. |
| 2012/0046965 A1 | 2/2012 | Ryan et al. |
| 2012/0056720 A1 | 3/2012 | Barvick et al. |
| 2012/0060216 A1 | 3/2012 | Chaudhri et al. |
| 2012/0078661 A1 | 3/2012 | Sheldon et al. |
| 2012/0084092 A1 | 4/2012 | Kozuch et al. |
| 2012/0095352 A1 | 4/2012 | Tran |
| 2012/0101846 A1 | 4/2012 | Gotthardt et al. |
| 2012/0112883 A1 | 5/2012 | Wallace et al. |
| 2012/0179479 A1 | 7/2012 | Waterson et al. |
| 2012/0185267 A1 | 7/2012 | Kamen et al. |
| 2012/0191476 A1 | 7/2012 | Reid et al. |
| 2012/0231959 A1 | 9/2012 | Elton et al. |
| 2012/0245464 A1 | 9/2012 | Tran |
| 2012/0251993 A1 | 10/2012 | Chidambaran et al. |
| 2012/0296671 A1 | 11/2012 | Simons-Nikolova et al. |
| 2013/0013333 A1 | 1/2013 | Gopinathan et al. |
| 2013/0034589 A1 | 2/2013 | Zhang et al. |
| 2013/0047113 A1 | 2/2013 | Hume et al. |
| 2013/0095459 A1 | 4/2013 | Tran |
| 2013/0096939 A1 | 4/2013 | Russell |
| 2013/0185097 A1 | 7/2013 | Sada et al. |
| 2013/0262357 A1 | 10/2013 | Amarasingham et al. |
| 2013/0304498 A1 | 11/2013 | Rangadass |
| 2013/0317844 A1 | 11/2013 | Hammond et al. |
| 2013/0318027 A1 | 11/2013 | Almogy et al. |
| 2014/0074509 A1 | 3/2014 | Amarasingham et al. |
| 2014/0095201 A1 | 4/2014 | Farooq et al. |
| 2014/0095420 A1 | 4/2014 | Chun et al. |
| 2014/0221765 A1 | 8/2014 | Harmon et al. |
| 2014/0249855 A1 | 9/2014 | Moore |
| 2014/0304200 A1 | 10/2014 | Wall |
| 2014/0350954 A1 | 11/2014 | Ellis et al. |
| 2015/0025329 A1 | 1/2015 | Amarasingham et al. |
| 2015/0025909 A1 | 1/2015 | Hayter |
| 2015/0066539 A1 | 3/2015 | Sheffer et al. |
| 2015/0106123 A1 | 4/2015 | Amarasingham et al. |
| 2015/0242586 A1 | 8/2015 | Kagen |
| 2016/0110523 A1 | 4/2016 | Francois |
| 2016/0203281 A1 | 7/2016 | Zalis et al. |
| 2016/0314256 A1 | 10/2016 | Su et al. |

OTHER PUBLICATIONS

Liu, et al., Integration of RFID and Wireless Sensor Networks, University of Birmingham, 2008, pp. 1-29 (Year: 2008).*
Stockman, Communication by Means of Reflected Power, Proceedings of the IRE, 1948, pp. 1196-1204 (Year: 1948).*

(56) References Cited

OTHER PUBLICATIONS

Escudero, J., et al., "Early Detection and Characterization of Alzheimer's Disease in Clinical Scenarios Using Bioprofile Concepts and K-Means," 33rd Annual International Conference of the IEEE EMBS, Aug. 30-Sep. 3, 2011, pp. 6470-6473.
Festersen, P.L., et al., "Re: Mind: A mobile application for bipolar disorder patients," Wireless Mobile Communication and Healthcare (Mobihealth), Nov. 3-5, 2014, pp. 343-346.
International Search Report and Written Opinion received in corresponding Patent Cooperation Treaty Application No. PCT/US2013/058159, dated Dec. 19, 2013, 8 pages.
Lorincz, K., et al., "Wearable Wireless Sensor Network to Assess Clinical Status in Patients with Neurological Disorders," Information Processing in Sensor Networks, Apr. 25-27, 2007, pp. 563-564.
Moorman, J. R., et al., "Predictive monitoring for early detection of subacute potentially catastrophic illnesses in critical care," 33rd Annual International Conference of the IEEE EMBS, Aug. 30-Sep. 3, 2011, pp. 5515-5518.
International Search Report and Written Opinion received in corresponding Patent Cooperation Treaty Application No. PCT/US2015/025200, dated Jul. 20, 2015, 8 pages.
International Search Report and Written Opinion received in corresponding Patent Cooperation Treaty Application No. PCT/US2015/025202, dated Jul. 16, 2015, 9 pages.
International Search Report and Written Opinion received in corresponding Patent Cooperation Treaty Application No. PCT/US2015/025203, dated Jul. 28, 2015, 9 pages.
International Search Report and Written Opinion received in corresponding Patent Cooperation Treaty Application No. PCT/US2015/025207, dated Jul. 28, 2015, 11 pages.
International Search Report and Written Opinion received in corresponding Patent Cooperation Treaty Application No. PCT/US2015/025205, dated Jul. 28, 2015, 8 pages.
International Search Report and Written Opinion received in corresponding Patent Cooperation Treaty Application No. PCT/US2015/025206, dated Jul. 16, 2015, 7 pages.
Alvarez, Carlos A., et al., "Predicting Out of Intensive Care Unit Cardiopulmonary Arrest or Death Using Electronic Medical Record Data," BMC Medical Informatics and Decision Making, Feb. 27, 2013, 11 pages.
Amarasingham, Ruben, et al., "Allocating Scarce Resources in Real-Time to Reduce Heart Failure Readmissions: A Prospective, Controlled Study," BMJ Quality and Safety Online First, Jul. 31, 2013, 10 pages.
Amarasingham, Ruben, et al., "An Automated Model to Identify Heart Failure Patients at Risk for 30-Day Readmission or Death Using Electronic Medical Record Data," Medical Care, vol. 48, No. 11, Nov. 2010, pp. 981-988.
Amarasingham, Ruben, et al., "Clinical Information Technology Capabilities in Four U.S. Hospitals, Testing a New Structural Performance Measure," Medical Care, vol. 44, No. 3, Mar. 2006, pp. 216-224.
Amarasingham, Ruben, et al., "Clinical Information Technologies and Inpatient Outcomes, a Multiple Hospital Study," Arch Intern Med, vol. 169, No. 2, Jan. 26, 2009, pp. 108-114.
Amarasingham, Ruben, et al., "Electronic Medical Record-Based Multicondition Models to Predict the Risk of 30 Day Readmission or Death Among Adult Medicine Patients: Validation and Comparison to Existing Models," BMC Medical Informatics and Decision Making, May 20, 2015, 8 pages.
Amarasingham, Ruben, et al., "Implementing Electronic Health Care Predictive Analytics: Considerations and Challengtes," Health Affairs, 33, No. 7, Jul. 2014, pp. 1148-1154.
Amarasingham, Ruben, et al., "A Rapid Admission Protocol to Reduce Emergency Department Boarding Times," BMJ Quality and Safety Online First, Feb. 8, 2010, pp. 200-204.
Bates, David W., et al., "Big Data in Health Care: Using Analytics to Identify and Manage High-Risk and High-Cost Patients," Health Affairs, 33, No. 7, Jul. 2014, pp. 1123-1131.
Bates, David W., "The Effects of Health Information Technology on Inpatient Care," Arch Intern Med, vol. 169, No. 2, Jan. 26, 2009, pp. 105-107.
Cohen, Glenn, et al., "The Legal and Ethical Concerns that Arise from Using Complex Predictive Analytics in Health Care,", Health Affairs, 33, No. 7, Jul. 2014, pp. 1139-1147.
Kansagara, Devan, et al., "Risk Prediction Models for Hospital Readmission, a Systematic Review," JAMA, vol. 306, No. 15, Oct. 19, 2011, pp. 1688-1698.
Makam, Anil N., et al., "Identifying Patients with Diabetes and the Earliest Data of Diagnosis in Real Time: An Electronic Health Record Case-Finding Algorithm," BMC Medical Informatics and Decision Making, Aug. 1, 2013, 7 pages.
McAlister, Finlay A., "Decreasing Readmissions: It Can Be Done But One Size Does Not Fit All," BMJ Quality and Safety Online First, Sep. 4, 2013, 3 pages.
Nehra, Mahendra S., et al., "Use of Administrative Claims Data for Identifying Patients with Cirrhosis," J Clin Gastroenterol, vol. 47, No. 5, May/Jun. 2013, pp. e50-e54.
Nijhawan, Ank E., "An Electronic Medical Record-Based Model to Predict 30-Day Risk of Readmission and Death Among HIV-Infected Inpatients," J Acquir Immune Defic Syndr, vol. 61, No. 3, Nov. 1, 2012, pp. 349-358.
Ram, Sudha, et al., "Predicting Asthma-Related Emergency Department Visits Using Big Data," IEEE Journal of Biomedical and Health Informatics, vol. 19, No. 4, Jul. 2015, pp. 1216-1223.
Singal, A.G., et al., "An Automated Model Using Electronic Medical Record Data Identifies Patients with Cirrhosis at High Risk for Readmission," Clinical Gastroenterology and Hepatology, vol. 11, No. 10, Oct. 2013, pp. 1335-1341.
Allen, Arthur, "The Frequent Flier" Program That Grounded a Hospital's Soaring Costs, www.politico.com, Dec. 18, 2017.
Baeza-Yates, Ricardo, et al, "Modem Informational Retrieval", ACM Press Books, 1999.
Baxt, William G., A Neural Computational Aid to the Diagnosis of Acute Myocardial Infarction, Annals of Emergency Medicine 39.4, Apr. 2002, pp. 366-373.
Birge, John R., et al., "Using Fuzzy Neural Network to Solve Short-Term Load Forecasting Problems", Dept. of Industrial & Operations Engineering, University of Michigan, Technical Report 96-20, 1996.
European Search Report received in European Application No. 13837780.9, dated Mar. 23, 2016.
European Search Report received in European Application No. 14827115.8, dated Feb. 21, 2017.
European Search Report received in European Application No. 14854100.6, dated May 18, 2017.
European Search Report received in European Application No. 15776758.3, dated Dec. 6, 2017.
European Search Report received in European Application No. 15777433.2, dated Jan. 2, 2018.
European Search Report received in European Application No. 15777472.0, dated Dec. 6, 2017.
European Search Report received in European Application No. 15777492.8, dated Dec. 11, 2017.
European Search Report received in European Application No. 15822510.2, dated Jun. 11, 2018.
European Search Report received in European Application No. 16858162.7, dated Jan. 18, 2019.
Healthit, Clinical Decision Support: More Than Just Alerts Tipsheet, Jul. 2015.
International Search Report and Written Opinion received in Patent Cooperation Treaty Application No. PCT/US2014/046029, dated Nov. 13, 2014.
International Search Report and Written Opinion received in Patent Cooperation Treaty Application No. PCT/US2014/060496, dated Feb. 3, 2015.
International Search Report and Written Opinion received in Patent Cooperation Treaty Application No. PCT/US2015/040335, dated Sep. 30, 2015.
International Search Report and Written Opinion received in Patent Cooperation Treaty Application No. PCT/US2016/048796, dated Nov. 29, 2016.

(56) References Cited

OTHER PUBLICATIONS

International Search Report and Written Opinion received in Patent Cooperation Treaty Application No. PCT/US2016/057773, dated Jan. 12, 2017.

Knutson, Dave, et al., "Predictive Modeling: A Guide for State Medicaid Purchasers", Center for Health Care Strategies, Aug. 2009.

Maran, Alberto, "Continuous Subcutaneous Glucose Monitoring in Diabetic Patients," Diabetes Care, vol. 25, No. 2, Feb. 2002, pp. 347-352.

Wikipedia, "Computer-Assisted Personal Interviewing", Mar. 31, 2018.

* cited by examiner

HOLISTIC HOSPITAL PATIENT CARE AND MANAGEMENT SYSTEM AND METHOD FOR AUTOMATED PATIENT MONITORING

RELATED APPLICATIONS

This patent application claims the benefit of U.S. Provisional Patent Application No. 61/978,058, filed on Apr. 10, 2014, and is a Continuation-In-Part Application of Clinical Predictive and Monitoring System and Method, Ser. No. 13/613,980, filed on Sep. 13, 2012. This patent application is also related to the following co-pending U.S. Non-Provisional Patent Applications:

U.S. Non-Provisional patent application Ser. No. 14/018, 514, entitled Clinical Dashboard User Interface System and Method, filed on Sep. 5, 2013;

U.S. Non-Provisional patent application Ser. No. 14/682, 705, entitled Holistic Hospital Patient Care and Management System and Method For Automated Staff Monitoring, filed on Apr. 9, 2015;

U.S. Non-Provisional patent application Ser. No. 14/682, 557, entitled Holistic Hospital Patient Care and Management System and Method For Automated Resource Management, filed on Apr. 9, 2015;

U.S. Non-Provisional patent application Ser. No. 14/682, 866, entitled Holistic Hospital Patient Care and Management System and Method For Enhanced Risk Stratification, filed on Apr. 9, 2015;

U.S. Non-Provisional patent application Ser. No. 14/682, 668, entitled Holistic Hospital Patient Care and Management System and Method For Situation Analysis Simulation, filed on Apr. 9, 2015;

U.S. Non-Provisional patent application Ser. No. 14/682, 745, entitled Holistic Hospital Patient Care and Management System and Method For Automated Facial Biological Recognition, filed on Apr. 9, 2015;

U.S. Non-Provisional patent application Ser. No. 14/682, 807, entitled Holistic Hospital Patient Care and Management System and Method For Telemedicine, filed on Apr. 9, 2015; and U.S. Non-Provisional patent application Ser. No. 14/682, 610, entitled Holistic Hospital Patient Care and Management System and Method For Patient and Family Engagement, filed on Apr. 9, 2015;

FIELD

The present disclosure relates to the healthcare industry, and more particularly to a holistic hospital patient care and management system and method.

BACKGROUND

A major challenge facing hospitals today is the timely identification of disease and appropriate engagement of patients and families required to offer patients appropriate care and treatment in order to avoid the progression of existing disease as well as the occurrence of a new adverse event, as well as to ensure that appropriate interventions and resources are available and deployed according to patients' needs.

Many national agencies, such as the Centers for Medicare and Medicaid Services (CMS), Institute for Healthcare Improvement (IHI), National Quality Forum (NQF), Agency for Healthcare Research and Quality (AHRQ), and Joint Commission have demonstrated their prioritization of high quality patient care through clearly articulated performance and quality measurement programs that incorporate disease-focused and patient-focused process and outcomes measures. These metrics are tied to standards that currently and will continue to impact the national performance-based incentive and penalty framework designed to realign efforts and focus on quality of care.

DETAILED DESCRIPTION

Figure 1:
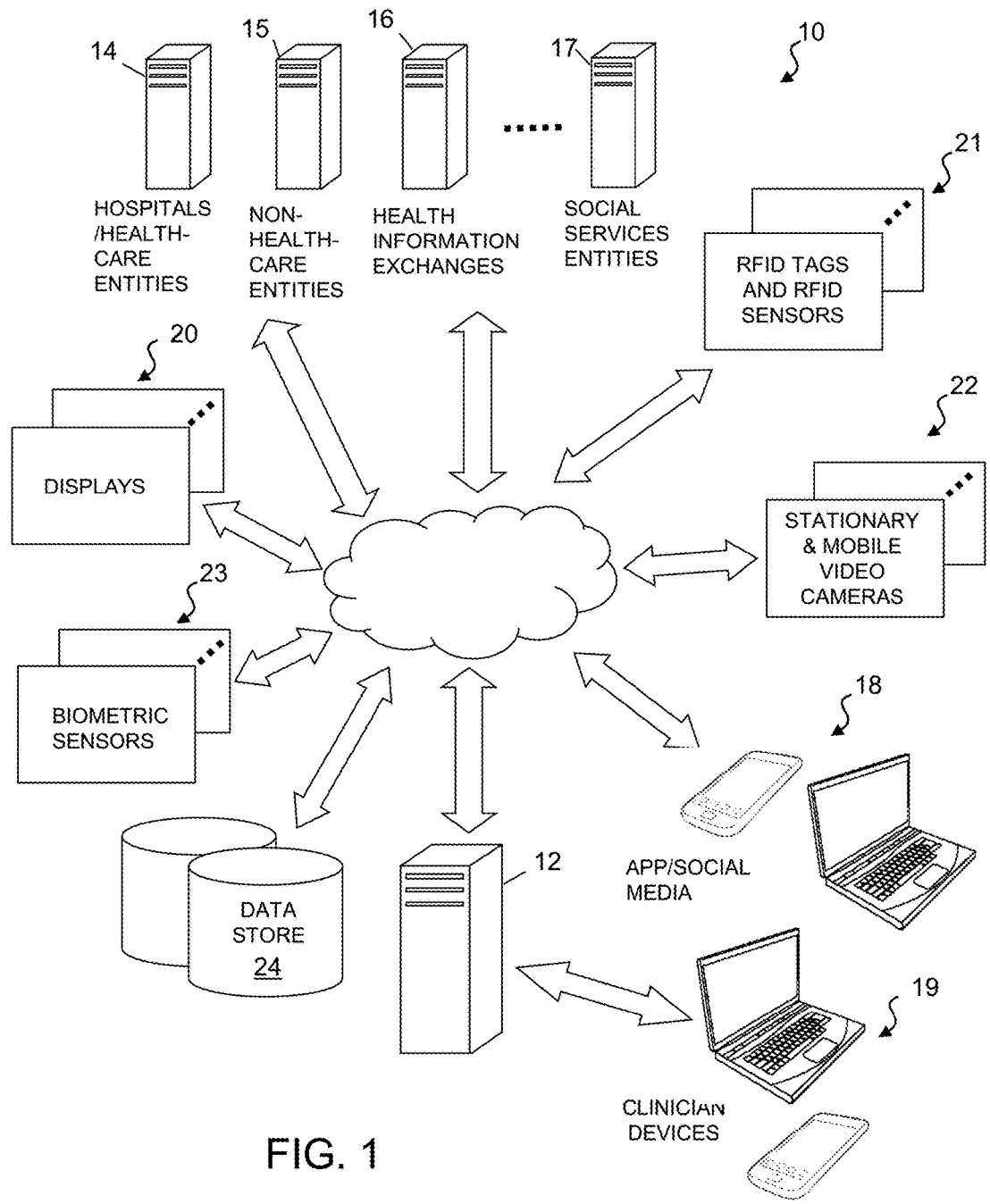
FIG. 1 is a simplified block diagram of an exemplary embodiment of a holistic hospital patient care and management system and method according to the present disclosure.

FIG. 1 is a simplified block diagram of an exemplary embodiment of a holistic hospital patient care and management system and method 10 according to the present disclosure. The holistic hospital patient care and management system 10 includes a computer system 12 adapted to receive a variety of clinical and non-clinical data relating to patients or individuals requiring care. The variety of data include real-time data streams and historical or stored data from hospitals and healthcare entities 14, non-health care entities 15, health information exchanges 16, and social-to-health information exchanges and social services entities 17, for example. These data are used to determine the likelihood of occurrence of an adverse event or disease classification via a risk score for selected patients so that they may receive more targeted intervention, treatment, and care that are better tailored and customized to their particular condition(s) and needs. The system 10 is most suited for identifying particular patients who require intensive inpatient and/or outpatient care to avert serious detrimental effects of certain diseases and to reduce hospital readmission rates. It should be noted that the computer system 12 may comprise one or more local or remote computer servers operable to transmit data and communicate via wired and wireless communication links and computer networks.

The data received by the holistic hospital patient care and management system 10 may include electronic medical records (EMR) data that is both clinical and non-clinical in nature. The EMR clinical data may be received from entities such as, but not limited to, hospitals, clinics, pharmacies, laboratories, and health information exchanges, and detail things such as, but limited to, vital signs and other physiological data; data associated with comprehensive or focused history and physical exams by a physician, nurse, or allied health professional; medical history (including utilization of various medical services); prior allergy and adverse medical reactions; family medical history; prior surgical history; emergency room records; medication administration records; culture results; dictated clinical notes and records; gynecological and obstetric history; mental status examination; vaccination records; radiological imaging exams; invasive visualization procedures; psychiatric treatment history; prior histological specimens; laboratory data; genetic information; physician's notes; networked devices and monitors (such as blood pressure devices and glucose meters); pharmaceutical and supplement intake information; and focused genotype testing.

The EMR non-clinical data may include, but is not limited to, social, behavioral, lifestyle, and economic data; history, type and nature of employment; medical insurance information; exercise information; (addictive) substance use; occupational chemical exposure; frequency of physician or health system contact; location of residences and frequency of residence changes over a specific time period; predictive screening health questionnaires such as the patient health questionnaire (PHQ); patient preference survey; personality tests; census and demographic data; neighborhood environments; diet; gender; marital status; education; proximity and number of family or care-giving assistants; address; housing status; social media data; and educational level. The non-clinical patient data may further include data entered by the patients, such as data entered or uploaded to a social media website.

Additional sources or devices of EMR data may provide, for example, procedure codes, lab/order results, medication assignments and changes, EKG results, radiology notes, daily weight readings, and daily blood sugar testing results. Data may be retrieved from sources such as hospitals, clinics, patient care facilities, patient home monitoring devices. Additionally, data may be provided by other available and relevant clinical or healthcare sources.

As shown in FIG. 1, patient data sources may include non-healthcare entities 15. These are entities or organizations that are not thought of as traditional healthcare providers. These entities 15 may provide non-clinical data that may include details around gender; marital status; education; community and religious organizational involvement; proximity and number of family or care-giving assistants; address; census tract location and census reported socioeconomic data for the tract; housing status; number of home address changes; requirements for governmental living assistance; number of scheduled (clinical) appointments which were kept and missed; independence on activities of daily living; hours of seeking medical assistance; location of medical services frequently sought after; sensory impairments; cognitive impairments; mobility impairments; educational level; employment; and economic status in absolute and relative terms to the local and national distributions of income; climate data; and health registries. Such data sources may provide additional insightful information about patient lifestyle/environment, such as the number of family members, marital status, any personal dependents, and health and lifestyle preferences that may influence individual health outcomes.

The holistic hospital patient care and management system 10 may further receive data from health information exchanges (HIE) 16. HIEs are organizations that mobilize healthcare information electronically across groups within a region, community or hospital system. HIEs are increasingly developed to share clinical and non-clinical patient data between healthcare entities within cities, states, regions, or within umbrella health systems. Data may be extracted from numerous sources such as hospitals, clinics, consumers, payers, physicians, labs, outpatient pharmacies, ambulatory centers, long-term acute care centers, skilled nursing facilities, and state or public health agencies.

A subset of HIEs connect healthcare entities to community organizations that do not specifically provide health services, such as non-governmental charitable organizations, social service agencies, and city agencies. The holistic hospital patient care and management system 10 may receive data from these social services organizations and social-to-health information exchanges 17, which may include, for example, information on daily living skills, availability of transportation to scheduled doctor's appointments, proximity of healthcare services, employment assistance, training, substance abuse rehabilitation, counseling or detoxification, rent and utilities assistance, homelessness status and receipt of services, medical follow-up, mental health services, meals and nutrition, food pantry services, housing assistance, temporary shelter, home health visits, domestic violence, medical appointment adherence, discharge instructions, prescriptions, medication instructions, neighborhood of residence, and ability to track referrals and appointments.

Another data source may include social media or social network services 18, such as FACEBOOK, TWITTER, GOOGLE+, and other similar websites. Such information sources 18 (represented by mobile phones and laptop computers) can provide information like number of family members, educational level, and relationship status, or may help to identify individuals who may be directly or indirectly involved with caring for a specific patient, and health and lifestyle preferences that may influence health outcomes. These social media data may be received from relevant social networking websites, at the expressed consent of the individual being evaluated, and some data may come directly from a user's computing devices (mobile phones, tablet computers, laptops, etc.) as the user enters status updates, at the expressed consent of the individual being evaluated. The above-enumerated non-clinical patient data may potentially provide a much more realistic and accurate depiction of the patient's overall health status and holistic healthcare environment. Augmented with such non-clinical patient data, the analysis and predictive modeling performed by the present system to identify patients at high-risk of readmission or an alternate adverse clinical event become much more robust and accurate. As always, prior to the collection and use of a patient's data, necessary patient consent and authorization are requested and received.

The system 10 is further adapted to receive and display user preferences and system configuration data from clinicians' computing devices (mobile devices, tablet computers, laptop computers, desktop computers, servers, etc.) 19 in a wired or wireless manner. These computing devices 19 are equipped to display a system dashboard and/or another graphical user interface to present data, reports, and alerts. The system is further in communication with a number of display monitors 20 mounted and located in a number of locations, including patient rooms, hallways, etc. A clinician (physicians, nurses, physician assistants, and other healthcare personnel) may use the system to access a number of patient data, including immediately generating a list of patients that have the highest congestive heart failure readmission risk scores using real-time data, e.g., top n numbers or top x %. A display in a patient's room may be used to provide care plan and/or discharge information to the patient and family. The graphical user interfaces are further adapted to receive the user's (healthcare personnel) input of preferences and configurations, etc. The data may be transmitted, presented, and displayed to the clinician/user in the form of web pages, web-based message, text files, video messages, multimedia messages, text messages, e-mail messages, and in a variety of suitable ways and formats.

The holistic hospital patient care and management system 10 further receives input and data from a number of additional sources, including RFID (Radio Frequency Identification) tags 21 that are worn, associated with, or affixed to patients, medical staff, hospital equipment, hospital instruments, medical devices, supplies, and medication. A plurality of RFID sensors 21 are distributed in the hospital rooms, hallways, equipment rooms, supply closets, etc. that are configured to detect the presence of RFID tags so that movement, usage, and location can be easily determined and monitored. Further, a plurality of stationary and mobile video cameras 22 are distributed in various strategic locations in the hospital to enable patient monitoring and identify biological changes in the patient. A plurality of sensors 23 including biometric sensors are also located in the hospital rooms. Additionally, the system 10 may receive input of ambient temperature and humidity of rooms and locations in the hospital, as well as the ability to control some aspects of the patient's environment, such as temperature and humidity.

Another source of location data may include Global Position System (GPS) data from a clinician's or patient's mobile telephones. The GPS coordinates may be received from the mobile devices and used to pinpoint a person's location if RFID data is not available. Using GPS data, a patient may be tracked and monitored during clinical visits, social services appointments, and visits and appointments with other care providers. The patient's location information may be used to monitor and predict patient utilization patterns of clinical services (e.g., emergency department, urgent care clinic, specialty clinic), social service organizations (e.g., food pantries, homeless shelters, counseling services), and the frequency of use of these services. These data may be used for analysis by the predictive model of the system.

As shown in FIG. 1, the holistic hospital patient care and management system 10 may receive data streamed real-time, or from historic or batched data from various data sources. Further, the system 10 may store the received data in a data store 24 or process the data without storing it first. The real-time and stored data may be in a wide variety of formats according to a variety of protocols, including CCD, XDS, HL7, SSO, HTTPS, EDI, CSV, etc. The data may be encrypted or otherwise secured in a suitable manner. The data may be pulled (polled) by the system 10 from the various data sources or the data may be pushed to the system 10 by the data sources. Alternatively or in addition, the data may be received in batch processing according to a predetermined schedule or on-demand. The data store 24 may include one or more secure local servers, memory, drives, and other suitable storage devices. Alternatively or in addition, the data may be stored in a data center in the cloud.

The computer system 12 may comprise a number of computing devices, including servers, that may be located locally or in a cloud computing farm. The data paths between the computer system 12 and the data store 24 may be encrypted or otherwise protected with security measures or transport protocols now known or later developed.

Figure 2:
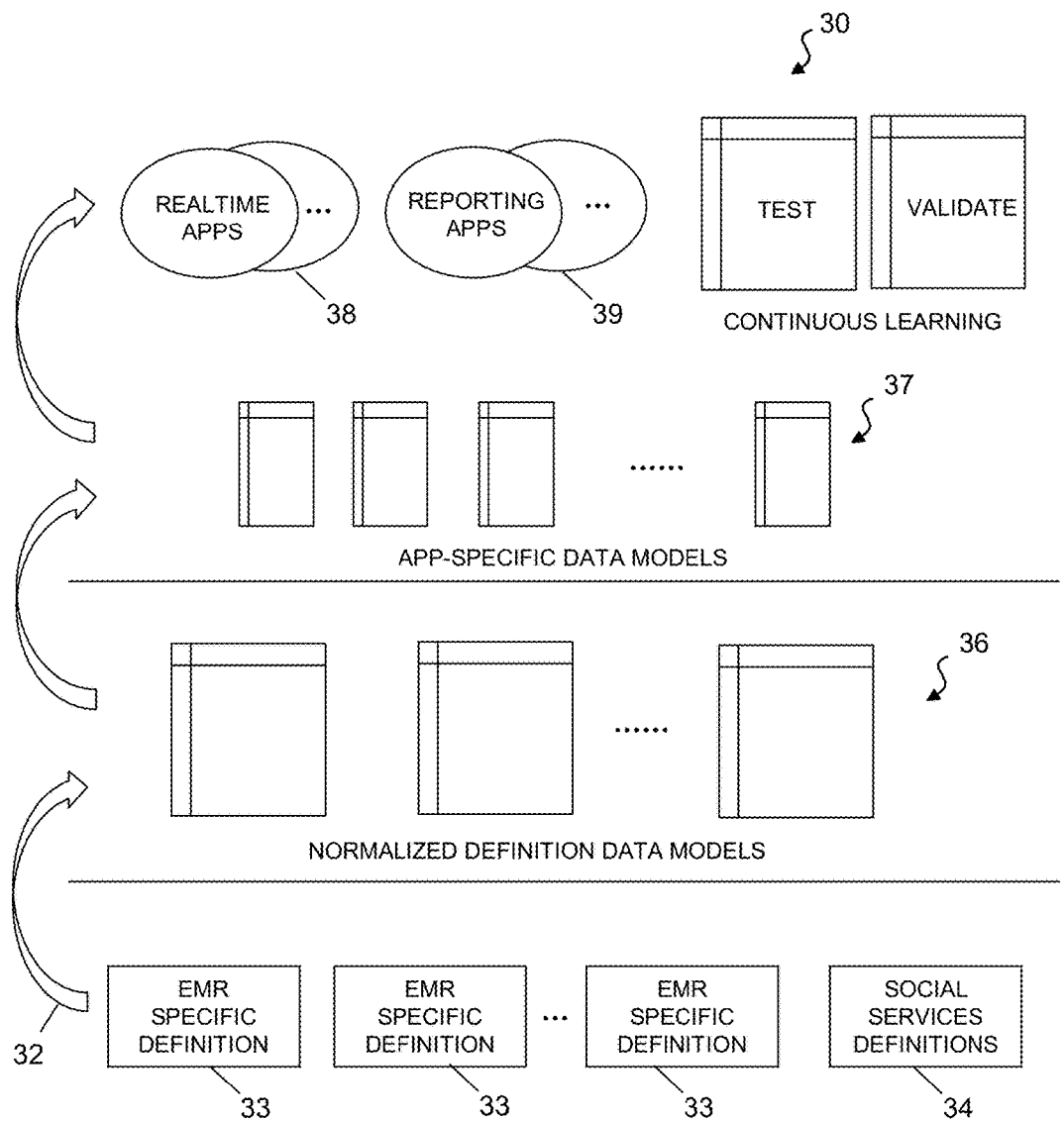
FIG. 2 is a simplified diagram of an exemplary architecture of the holistic hospital patient care and management system and method according to the present disclosure.

FIG. 2 is a simplified diagram of an exemplary architecture 30 of the holistic hospital patient care and management system and method 10 according to the present disclosure. At the bottom layer, data 32 from the information sources are in a plurality of EMR-specific data definitions 33, and social service data definitions 34. Each clinical or non-clinical (social service) institution or entity may define the format for its own data and database, which is typically different from that of other entity or organization's database formats. The EMR-specific data definitions 33 are mapped or translated to a number of data models 36 used by the system 10. It is preferable that the system's data models 36 are normalized, or in other words, organized or arranged to minimize redundancy. The system's data models 36 are further converted or mapped to a number of application-specific data models 37 that are developed for the system's software applications, such as real time applications 38 and reporting applications 39. The system further continuously perform ongoing model maintenance to ensure that optimal performance is achieved.

Figure 3:
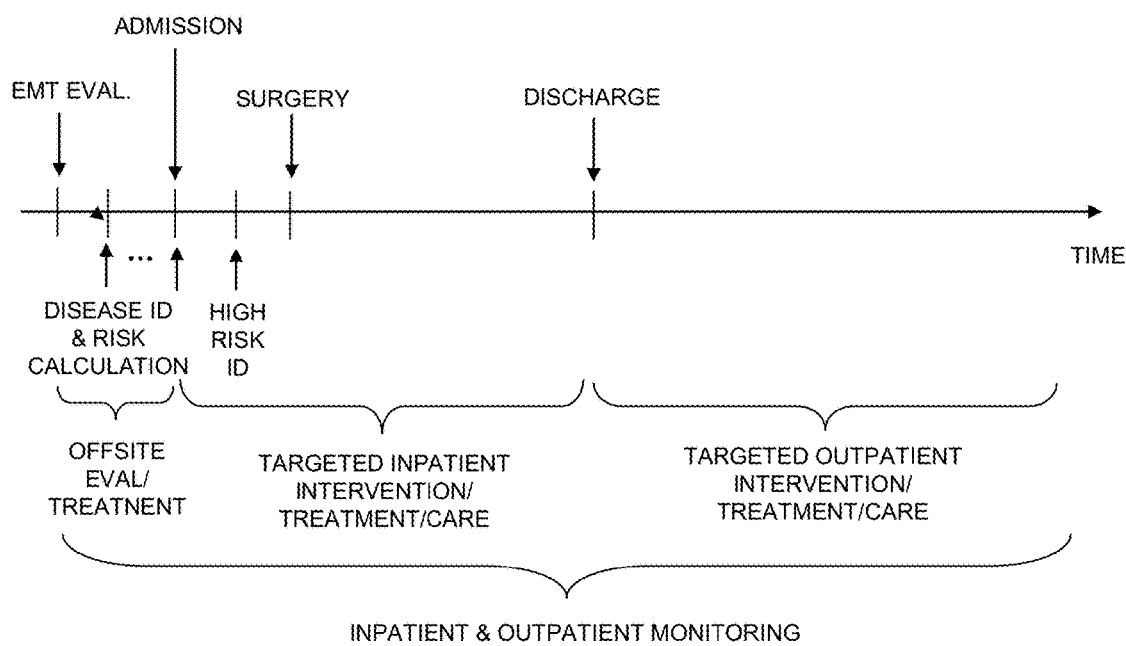
FIG. 3 is a timeline diagram depicting the application of the holistic hospital patient care and management system and method during a patient's progression from hospital admission to post-discharge according to the present disclosure.

FIG. 3 is a timeline diagram of an exemplary embodiment of a clinical predictive and monitoring subsystem 40 of the holistic hospital patient care and management system and method 10 according to the present disclosure. The timeline diagram is used to illustrate how the holistic hospital patient care and management system and method 10 may be applied to a typical patient experiencing congestive heart failure as an example. A majority of U.S. hospitals struggle to contain readmission rates related to congestive heart failure. Though numerous studies have found that some combination of careful discharge planning, care provider coordination, and intensive counseling can prevent subsequent re-hospitalizations, success is difficult to achieve and sustain at the typical U.S. hospital. Enrolling all heart failure patients into a uniform, high intensity care transition program requires a depth of case management resources that is out of reach for many institutions, particularly safety-net hospitals. The clinical predictive and monitoring subsystem and method 40 is adapted to accurately stratify risk for certain diseases and conditions such as 30-day readmission among congestive heart failure patients.

When Emergency Medical Technicians (EMTs) are summoned upon a patient complaining of chest pains in their home, the ideal protocol is that the EMTs assess the patient, takes vital signs, and via video cameras worn by the EMT (using, e.g., glasses-mounted camera or shoulder-mounted camera), transmits a video of the patient to appropriate medical personnel at the hospital. Together with the physician, the EMTs recognize and validate that the patient may be suffering from a heart attack, and prepares to administer care to stabilize the patient. All past medical history and data of the patient become accessible from the hospital's EMR to the EMT personnel, who notes a patient allergy to aspirin prior to administration of any therapy. The EMT is able to deliver appropriate care to the patient, and is in constant communication with the on-site physician who is awaiting the patient's arrival. Within a certain time of a patient's admission to the hospital, stored historical and real-time patient data are analyzed by the clinical predictive and monitoring system and method to confirm both the likelihood of diagnosis of a specific disease(s) and the likelihood of occurrence of certain subsequent adverse events related to the patient, such as congestive heart failure (readmission), taking into account the most recent adverse event as well. The processes for disease identification and risk score calculation are described in more detail below. Bypass surgery may be identified by physicians as necessary to alleviate angina and reduce the risk of death. During surgery, the system transmits the patient's conditions and status on a real time basis to the patient's family. Therefore, throughout the patient's stay in the hospital as well as after discharge, the holistic hospital patient care and management system 10 continually monitors the patient's condition, collects patient data in real-time, arranges for efficient delivery of care, manages the hospital's resources and supplies, and communicates timely or real time information to healthcare providers and the patient's family.

Figure 4:
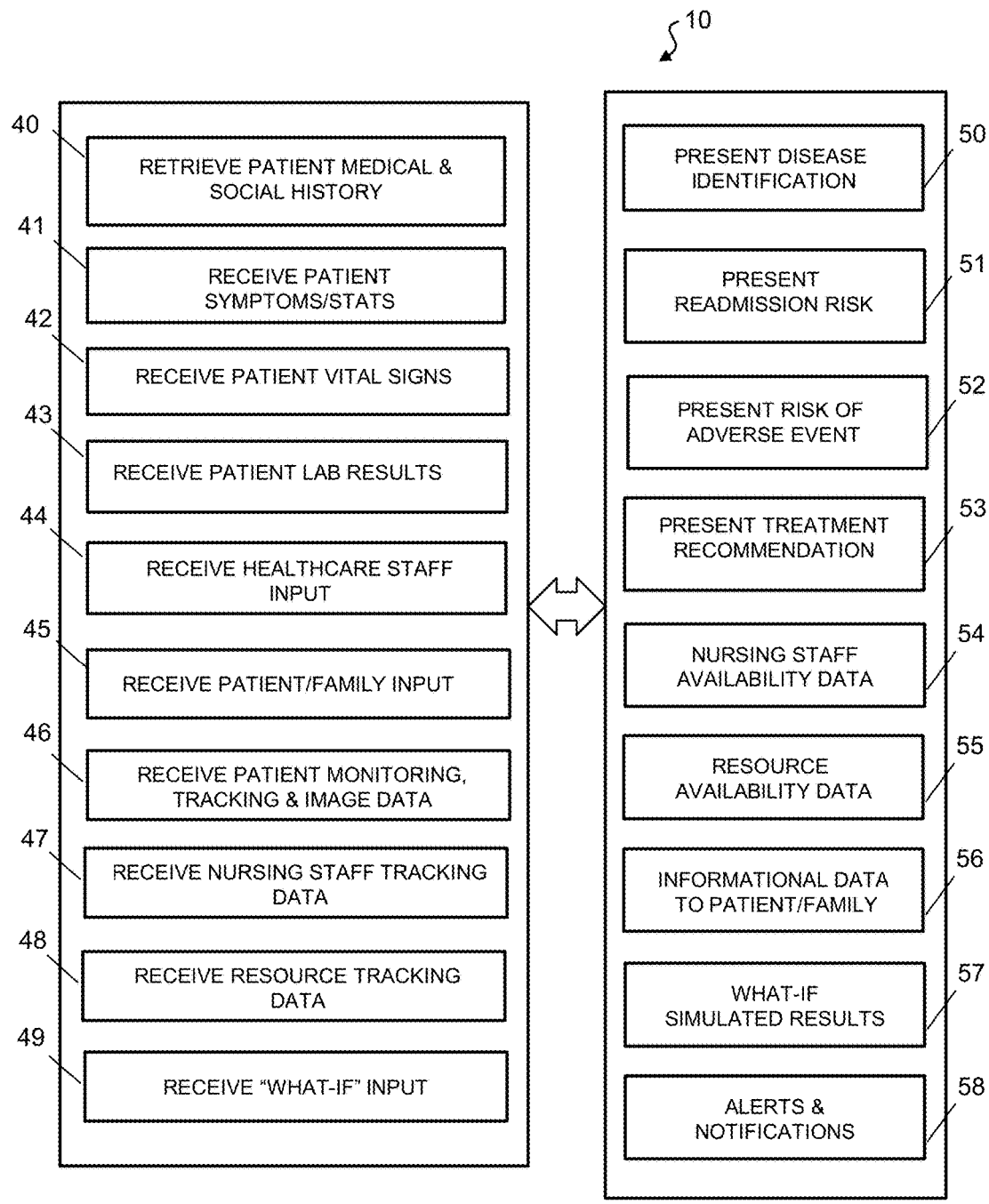
FIG. 4 is a simplified logical block diagram of an exemplary embodiment of a clinical predictive and monitoring system and method, by detailed inputs and outputs, according to the present disclosure.

FIG. 4 is a simplified logical block diagram further illustrating the information input into and output from the holistic hospital patient care and management system and method 10. As noted above, the system 10 retrieves and uses patient data that include real-time and historical clinical and non-clinical data 40. When a patient first presents at a medical facility, such as an emergency department of a hospital, his or her symptoms and information 41 such as height, weight, personal habits (e.g., smoking/non-smoking), current medications, etc. are noted and entered by the medical staff into the system 10. Additionally, the system 10 regularly receives the patient's clinical information, including vital signs 42, (e.g., blood pressure, pulse rate, and body temperature). The healthcare staff may order lab tests and these results 43 are also transmitted or entered into the system 10. The healthcare staff's input 44, including notes, diagnosis, and prescribed treatment are entered into the system 10 as well. Further, the patient and/or family member may be given a tablet, laptop computer or use a mobile telephone to access custom applications designed to facilitate input 45 around the patient's preferences (dietary preferences, preferred rounding time, complaints about medications, etc.), comments, feedback, and current (clinical) status during the patient's stay at the hospital, as well as after discharge from the hospital. Additionally, the hospital is equipped with a variety of tools, equipment and technology that are configured to monitor the patient's vital signs, wellbeing, presence, location, and other parameters. These may include RFID tags and sensors, or GPS systems, for example, for location monitoring. Additionally, cameras may be mounted in the patient room, hallways, emergency department, radiology department, and other parts of the hospital to generate still and moving video images of the patient. The patient monitoring, location tracking, and image data 46 from these devices are also provided as input to the system.

Healthcare staff, such as physicians and nurses may also carry ID badges with embedded RFID tags that enable their location, movement, and availability within the hospital to be tracked. This healthcare staff tracking information 47 is provided as input to the system. Further, for resource management, the availability of certain hospital resources is also tracked and monitored, with occupied and free resources noted appropriately. Other resources such as equipment, medication, supplies may include RFID tags that are used to track their location (shelf, room, storage, department, etc.), use, and availability. The system 10 also receives this resource tracking data 48 from the various sensors distributed throughout the facilities.

In addition to the above data that are received by the system 10, another input includes "What-If" scenarios 49 intended to simulate outcomes given specific parameters and conditions as entered by a member of the operations group of the hospital or health facility. The user may select one or more constraints, such as staffing level, hours of operation, the number of new patients, the number of available patient beds, the availability of certain medical equipment, the amount of supplies, and simulation time period, varying values to create a simulated scenario for purposes of generating possible outcomes. The system 10 may further generate recommendations based on the simulated outcome to avoid adverse events or unfavorable results.

All of the above-described input data including the clinical and non-clinical patient data are continually received, collected, and/or polled by the system 10 whenever they become available and are used in analysis for a number of output data and results. The data may be presented in numerical format, graphical format, textual format, etc. The system 10 is configured to provide disease identification 50, risk identification 51, adverse event identification 52, and recommended treatment and therapy 53 on a real-time or near real-time basis. The information presented by the system 10 preferably includes an identification of one or more diseases that the patient has, whether the patient is at risk for readmission due to a particular condition, and whether there is a risk of the occurrence of one or more adverse events. The system 10 includes a predictive model that provides treatment or therapy recommendations based on the patient's data (e.g., medical history, symptoms, current vital signs, lab results, and the clinician's notes, comments, and diagnosis), and forms the fundamental technology for identification of diseases, readmission risk, adverse events, and situation simulation. Additionally, the system 10 is configured to generate a course of treatment or therapy recommendations for the patient based on disease, risk, and adverse event identification. Disease identification, risk identification, adverse event identification, and patient care surveillance information are displayed, reported, transmitted, or otherwise presented to healthcare personnel based on the user's identity or in a role-based manner. In other words, a patient's data and analysis is available to a particular user if that user's identity and/or role is relevant to the patient's care and treatment. For example, the attending physician and the nursing staff may access the patient data as well as receive automatically-generated alerts regarding the patient's status, and missed or delayed treatment. An attending physician may only have access to information for patients under his/her care, but an oncology department head may have access to data related to all of the cancer patients admitted at the facility, for example. As another example, the hospital facility's chief medical officer and chief nursing officer may have access to all of the data about all of the patients treated at the facility so that innovative procedures or policies may be implemented to prevent or minimize adverse events.

Further, the system 10 provides information on the availability of the healthcare staff 54, such as current nurse load for efficient resource allocation purposes. The system 10 also has an inventory of available equipment, supplies, and other resources 55, and can quickly pinpoint the location of available and required medical resources.

Another form of information or data presented by the system 10 is information about the disease, therapy, and care plan useful to the patient and family 56. The patient and family may also have access to the patient's medical information, lab results, prescriptions, etc.

The system 10 also provides what-if simulation results 57 in response to the variations on some input parameters including staffing level, hours of operation, resource availability, current patient census, etc.

The system 10 also outputs various notifications and alerts 58 to the appropriate personnel so that proper action can be taken regarding the patient's treatment and care. Any of the functions described above may include an alert and notification output that can immediately present and push information to a user. For example, if a patient's lab results or vitals became available and it suggests that the patient's condition is deteriorating, an alert is immediately generated and transmitted to the attending physician and/or nursing staff.

Figure 5:
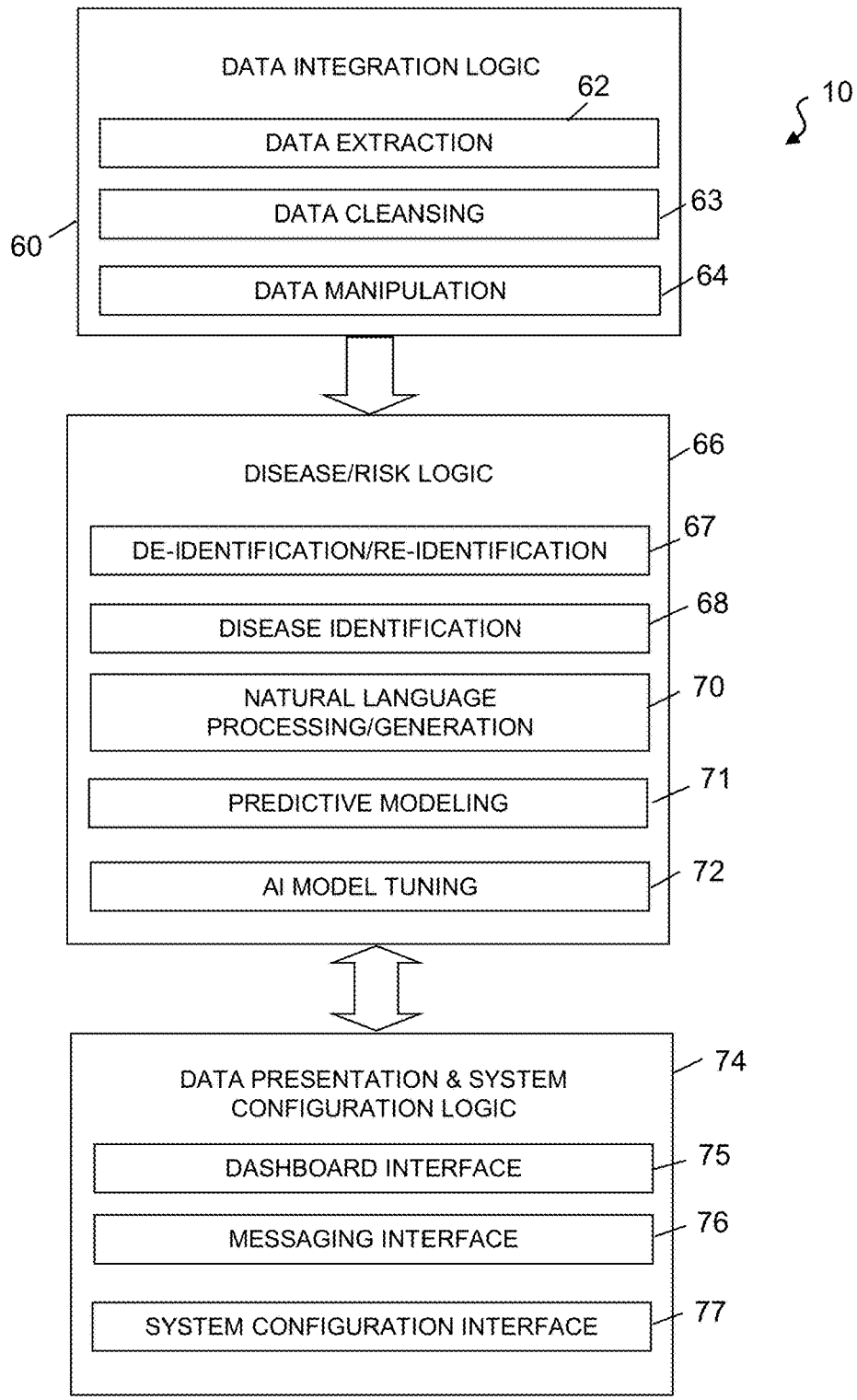
FIG. 5 is a simplified logical block diagram illustrating the conceptual data integration, disease/risk, and data presentation and system configuration logic of an exemplary embodiment of the holistic hospital patient care and management system and method according to the present disclosure.

FIG. 5 is a simplified logical block diagram of an exemplary embodiment of the holistic hospital patient care and management system and method 10 according to the present disclosure. The holistic hospital patient care and management system and method 10 receives and extracts data from many disparate sources in myriad formats pursuant to different protocols, the incoming data must first undergo a multi-step process before they may be properly analyzed and utilized. The holistic hospital patient care and management system and method 10 includes a data integration logic module 60 that further includes a data extraction process 62, a data cleansing process 63, and a data manipulation process 64. It should be noted that although the data integration logic module 60 is shown to have distinct processes 62-64, these are done for illustrative purposes only and these processes may be performed in parallel, iteratively, and interactively.

The data extraction process 62 extracts clinical and non-clinical data from data sources in real-time or batch files using hospital-accepted protocols. Preferably in real-time, the data cleansing process 63 "cleans" or pre-processes the data, putting structured data in a standardized format and preparing unstructured text for natural language processing (NLP) to be performed in the disease/risk logic module 66 described below. The system 10 may also receive "clean" data or previously processed data and convert them into desired formats (e.g., text date field converted to numeric for calculation purposes).

The data manipulation process 64 may analyze the representation of a particular data feed against a meta-data dictionary and determine if a particular data feed should be re-configured or replaced by alternative data feeds. For example, a given hospital EMR may store the concept of "maximum creatinine" in different ways. The data manipulation process 64 may make inferences in order to determine which particular data feed(s) from the EMR would most accurately represent the whole concept of "creatinine" as defined in the meta-data dictionary and whether a feed would need particular re-configuration to arrive at the maximum value (e.g., select highest value).

The data integration logic module 60 then passes the pre-processed data to a disease/risk logic module 66. The disease/risk logic module 66 is operable to calculate a risk score associated with a specific disease or condition for each patient and subsequently identify those patients who should receive more targeted intervention and care as a result of the assigned risk score (e.g., patient's risk of readmission for a particular condition, patient's risk of the occurrence of one or more adverse events). The disease/risk logic module 66 includes a de-identification/re-identification process 67 that is adapted to remove all protected identifying information according to HIPAA standards before the data is transmitted over the Internet. It is also adapted to re-identify the data. Protected identifying information that may be removed and added back later may include, for example, name, phone number, facsimile number, email address, social security number, medical record number, health plan beneficiary number, account number, certificate or license number, vehicle number, device number, URL, all geographical subdivisions smaller than a state identifier, including street address, city, county, precinct, zip code, and their equivalent geocodes (except for the initial three digits of a zip code, if according to the current publicly available data from the Bureau of the Census), Internet Protocol number, biometric data, and any other unique identifying number, characteristic, or code.

The disease/risk logic module 66 further includes a disease identification process 68. The disease identification process 68 is configured to identify one or more diseases or conditions of interest for each patient. The disease identification process 68 considers data such as, but not limited to, lab orders, lab values, clinical text and narrative notes, and other clinical and historical information to determine the probability that a patient has a particular disease. Additionally, during disease identification, natural language processing is conducted on unstructured clinical and non-clinical data to determine the potential disease(s) that the physician believes are likely to be diagnosed for the patient. This process 68 may be performed iteratively over the course of multiple days to establish a higher confidence in identifying the disease as the attending physician becomes more certain in the diagnosis. When a patient is identified to have a particular disease, the patient is identified in a disease list for that ailment. Where new or updated patient data may not support a previously identified disease, the system would automatically remove the patient from that disease list.

The disease/risk logic 66 includes a hybrid model of natural language processing and generation 70, which combines a rule-based model and a statistically-based learning model. During natural language processing 70, raw unstructured data, for example, physicians' notes and reports, first go through a process called tokenization. The tokenization process divides the text, in the form of raw unstructured data, into basic units of information in the form of single words or short phrases by using defined separators such as punctuation marks, spaces, or capitalizations. Using the rule-based model, these basic units of information are identified in a meta-data dictionary and assessed according to predefined rules that determine meaning Using the statistical-based learning model, the disease identification process 68 quantifies the relationship and frequency of word and phrase patterns and then processes them using statistical algorithms. Using machine learning, the statistical-based learning model develops inferences based on repeated patterns and relationships. The disease identification process 68 performs a number of complex natural language processing functions including text pre-processing, lexical analysis, syntactic parsing, semantic analysis, handling multi-word expression, word sense disambiguation, and other functions.

For example, if a physician's notes include the following: "55 yo m c h/o dm, cri. now with adib rvr, chfexac, and rle cellulitis going to 10 W, tele." The data integration logic 60 is operable to translate these notes as: "Fifty-five-year-old male with history of diabetes mellitus, chronic renal insufficiency now with atrial fibrillation with rapid ventricular response, congestive heart failure exacerbation and right lower extremity cellulitis going to 10 West and on continuous cardiac monitoring."

Continuing with the prior example, the disease identification process 68 is adapted to further ascertain the following: 1) the patient is being admitted specifically for atrial fibrillation and congestive heart failure; 2) the atrial fibrillation is severe because rapid ventricular rate is present; 3) the cellulitis is on the right lower extremity; 4) the patient is on continuous cardiac monitoring or telemetry; and 5) the patient appears to have diabetes and chronic renal insufficiency.

The disease component/risk logic module 66 further comprises a predictive modeling process 71 that is adapted to predict the risk of being diagnosed with particular diseases or developing an adverse event of interest according to one or more predictive models. For example, if a hospital desires to determine the level of risk for future readmission for heart failure, the heart failure predictive model may be selected for processing patient data. However, if the hospital desires to determine the risk levels for readmission for all internal medicine patients for any cause, an all-cause readmissions predictive model may be used to process the patient data. As another example, if the hospital desires to identify those patients at risk for short-term and long-term diabetic complications, the diabetes disease identification component may be used to target those patients. Other predictive models may include HIV readmission, risk for cardio-pulmonary arrest, kidney disease progression, acute coronary syndrome, pneumonia, cirrhosis, colon cancer pathway adherence, and others.

Continuing to use the prior example, the predictive model for congestive heart failure may take into account a set of risk factors, such as laboratory and vital sign variables including: albumin, total bilirubin, creatine kinase, creatinine, sodium, blood urea nitrogen, partial pressure of carbon dioxide, white blood cell count, troponin-I, glucose, internationalized normalized ratio, brain natriuretic peptide, pH, temperature, pulse, diastolic blood pressure, and systolic blood pressure. Further, non-clinical factors are also considered. The predictive model is configured to each hospital based on a retrospective data analysis conducted to tune the model to fit the unique characteristics of each individual hospital. In this manner, the system is able to stratify, in real-time, the risk of each patient that arrives at a hospital or another healthcare facility. Therefore, those patients at the highest risk are automatically identified so that targeted intervention and care may be instituted. One output from the disease component/risk logic module 66 includes the risk scores of all the patients for particular potential disease diagnosis or adverse event. In addition, the module 66 may rank the patients according to the risk scores, and provide a sortable list to facilitate prioritizing the patients needing the most resources. For example, a hospital may desire to identify the top 20 patients most at highest risk for congestive heart failure readmission, and the top 5% of patients most at highest risk for cardio-pulmonary arrest in the next 24 hours. Other diseases and adverse events that may be identified through risk stratification using predictive modeling include, HIV readmission, diabetes identification, kidney disease progression, colorectal cancer continuum screening, meningitis management, acid-base management, anticoagulation management, etc.

The natural language generation module 70 is adapted to receive the unstructured clinical information for a patient, and "translate" that data to present the textual evidence that the patient is at high-risk for a specific disease. In this manner, the intervention coordination team may better formulate the targeted inpatient and outpatient intervention and treatment plan to address the patient's potential specific situation.

The disease component/risk logic module 66 further includes an artificial intelligence (AI) model tuning process 72. The artificial intelligence model tuning process 72 utilizes adaptive self-learning capabilities using machine learning technologies. The capacity for self-reconfiguration enables the system and method 10 to be sufficiently flexible and adaptable to detect and incorporate trends or differences in the underlying patient data or population that may affect the predictive accuracy of a given algorithm. The artificial intelligence model tuning process 72 may periodically retrain a selected predictive model for improved accurate outcome to allow for selection of the most accurate statistical methodology, variable count, variable selection, interaction terms, weights, and intercept for a local health system or clinic. The artificial intelligence model tuning process 72 may automatically modify or improve a predictive model in three exemplary ways. First, it may adjust the predictive weights of clinical and non-clinical variables without human supervision. Second, it may adjust the threshold values of specific variables without human supervision. Third, the artificial intelligence model tuning process 72 may, without human supervision, evaluate new variables present in the data feed but not used in the predictive model, which may result in improved accuracy. The artificial intelligence model tuning process 72 may compare the actual observed outcome of the event to the predicted outcome then separately analyze the variables within the model that contributed to the incorrect outcome. It may then re-weigh the variables that contributed to this incorrect outcome, so that in the next reiteration those variables are less likely to contribute to a false prediction. In this manner, the artificial intelligence model tuning process 72 is adapted to reconfigure or adjust the predictive model based on the specific clinical setting or population in which it is applied. Further, no manual reconfiguration or modification of the predictive model is necessary. The artificial intelligence model tuning process 72 may also be useful to scale the predictive model to different health systems, populations, and geographical areas in a rapid timeframe.

As an example of how the artificial intelligence model tuning process 72 functions, the sodium variable coefficients may be periodically reassessed to determine or recognize that the relative weight of an abnormal sodium laboratory result on a new population should be changed from 0.1 to 0.12. Over time, the artificial intelligence model tuning process 72 examines whether thresholds for sodium should be updated. It may determine that in order for the threshold level for an abnormal sodium laboratory result to be predictive for readmission, it should be changed from, for example, 140 to 136 mg/dL. Finally, the artificial intelligence model tuning process 72 is adapted to examine whether the predictor set (the list of variables and variable interactions) should be updated to reflect a change in patient population and clinical practice. For example, the sodium variable may be replaced by the NT-por-BNP protein variable, which was not previously considered by the predictive model.

The results from the disease component/risk logic module 66 are provided to the designated medical staff, such as the intervention coordination team and other care providers, by a data presentation and system configuration logic module 74. The data presentation logic module 74 includes a dashboard interface 75 that is adapted to provide information on the performance of the system and method 10. A user (e.g., medical staff, administrator, and intervention coordination team) is able to find specific data they seek through simple and clear visual navigation cues, icons, windows, and devices. The interface may further be responsive to audible commands, for example. Because the number of patients a hospital admits each day can be overwhelming, a simple graphical interface that maximizes efficiency and reduces user navigation time is especially desirable. The visual cues are preferably presented in the context of the problem being evaluated (e.g., readmissions, out-of-ICU, cardiac arrest, diabetic complications, among others).

The dashboard user interface 75 allows interactive requests for a variety of views, reports and presentations of extracted data and risk score calculations from an operational database within the system, including for example, summary views of a list of patients in a specific care location; graphical representations of the data for a patient or population over time; comparison of incidence rates of predicted events to the rates of prediction in a specified time frame; summary text clippings, lab trends and risk scores on a particular patient for assistance in dictation or preparation of history and physical reports, daily notes, sign-off continuity of care notes, operative notes, discharge summaries, continuity of care documents to outpatient medical practitioners; automated order generation of orders authorized by a care provider's healthcare environment and state and national guidelines to be returned to the practitioner's office, outside healthcare provider networks or for return to a hospital or practices electronic medical record; aggregation of the data into frequently used medical formulas to assist in care provision including but not limited to: acid-base calculation, MELD score, Child-Pugh-Turcot score, TIMI risk score, CHADS score, estimated creatinine clearance, Body Surface area, Body Mass Index, adjuvant, neoadjuvant and metastatic cancer survival nomograms, MEWS score, APACHE score, SWIFT score, NIH stroke scale, PORT score, AJCC staging; and publishing of elements of the data on scanned or electronic versions of forms to create automated data forms.

The data presentation and system configuration logic module 74 further includes a messaging interface 76 that is adapted to generate output messaging code in forms such as HL7 messaging, text messaging, e-mail messaging, multimedia messaging, web pages, web portals, REST, XML, computer generated speech, constructed document forms containing graphical, numeric, and text summary of the risk assessment, reminders, and recommended actions. The interventions generated or recommended by the system and method 10 may include: risk score report to the primary physician to highlight risk of readmission for their patients; score report via new data field input into the EMR for use by population surveillance of entire population in hospital, covered entity, accountable care population, or other level of organization within a healthcare providing network; comparison of aggregate risk of readmissions for a single hospital or among hospitals within a system to allow risk-standardized comparisons of hospital readmission rates; automated incorporation of score into discharge summary template, continuity of care document (within providers in the inpatient setting or to outside physician consultants and primary care physicians), HL7 message to facility communication of readmission risk transition to nonhospital physicians; and communicate subcomponents of the aggregate social-environmental score, clinical score and global risk score. These scores would highlight potential strategies to reduce readmissions including, but not limited to: generating optimized medication lists, or alternate medication therapy management practices; allowing pharmacies to identify those medication on formulary to reduce out-of-pocket cost and improve outpatient compliance with the pharmacy treatment plan; flagging patient education around such topics like maintaining a specific diet, identifying alternate modes of transportation; identifying alternate housing options (e.g., nursing home placement, transitional housing, or Section 8 HHS housing assistance) or financial assistance programs.

This output may be transmitted wirelessly or via LAN, WAN, the Internet, and delivered to healthcare facilities' electronic medical record stores, user electronic devices (e.g., pager, text messaging program, mobile telephone, tablet computer, mobile computer, laptop computer, desktop computer, and server), health information exchanges, and other data stores, databases, devices, and users. The system and method 10 may automatically generate, transmit, and present information such as high-risk patient lists with risk scores, natural language generated text, reports, recommended therapies, alerts, Continuity of Care Documents, flags, appointment reminders, telemedicine video communications, simulation results and recommendations, healthcare staff location and availability, and patient/family surveys or questionnaires.

The data presentation and system configuration logic module 74 further includes a system configuration interface 77. Local clinical preferences, knowledge, and approaches may be directly provided as input to the predictive models through the system configuration interface 77. This system configuration interface 77 allows the institution or health system to set or reset variable thresholds, predictive weights, and other parameters in the predictive model directly. The system configuration interface 77 preferably includes a graphical user interface designed to minimize user navigation time.

Figure 6:
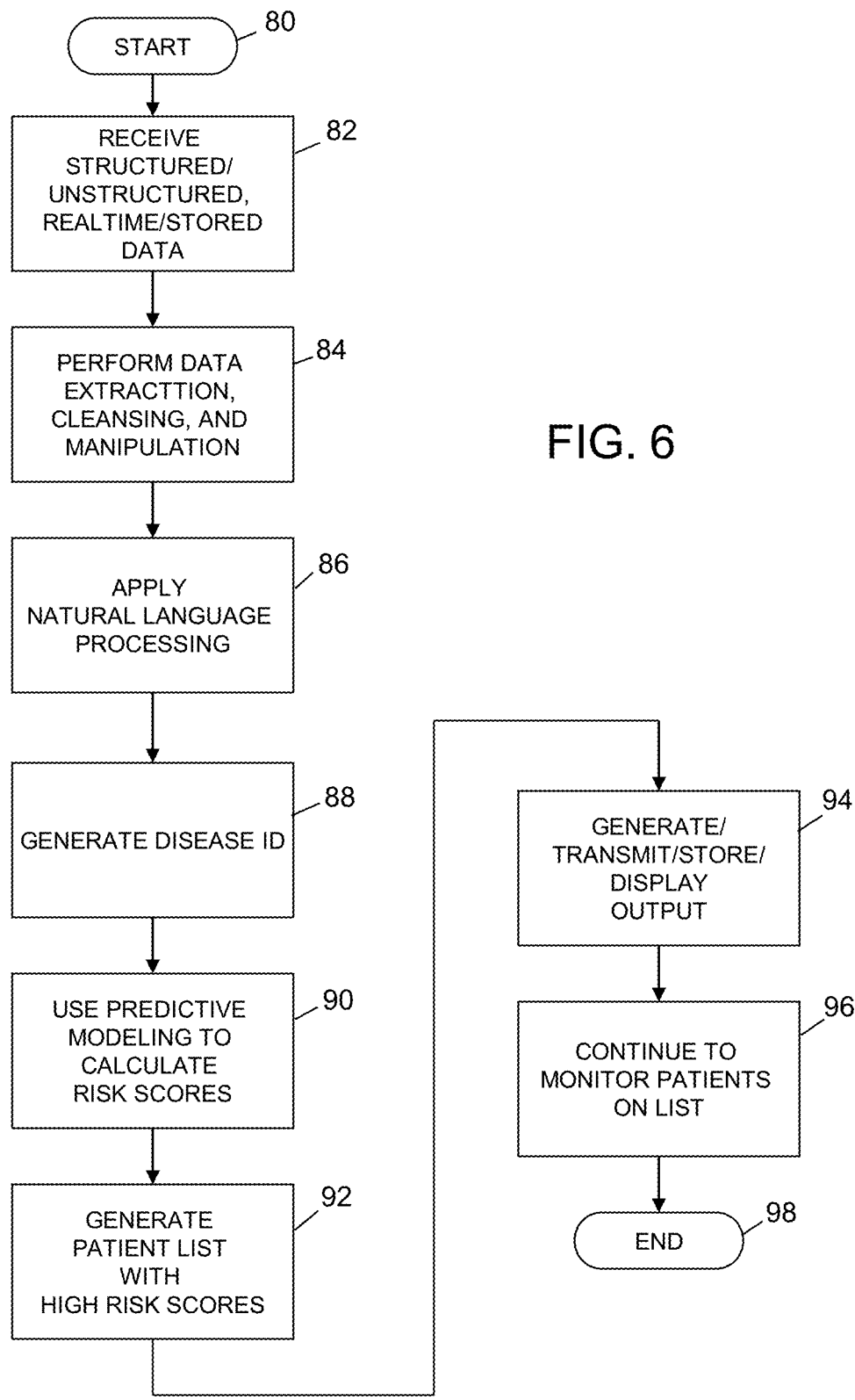
FIG. 6 is a simplified flowchart/block diagram, illustrating the process of predictive analytics based on data inputs and outputs throughout a patient's care continuum, of an exemplary embodiment of a clinical predictive and monitoring method according to the present disclosure.

FIG. 6 is a simplified flowchart of an exemplary embodiment of a clinical predictive and monitoring method 80 according to the present disclosure. The method 80 receives structured and unstructured clinical and non-clinical data related to specific patients from a variety of sources and in a number of different formats, as shown in block 82. These data may be encrypted or protected using data security methods now known or later developed. In block 84, the method 80 pre-processes the received data: data extraction, data cleansing, and data manipulation. Other data processing techniques now known and later developed may be utilized. In block 86, data processing methods such as natural language processing and other suitable techniques may be used to translate or otherwise make sense of the unstructured data. In block 88, by analyzing the pre-processed data, one or more potential diseases or adverse events of interest as related to each patient are identified. In block 90, the method 80 applies one or more predictive models to further analyze the data and calculate one or more risk scores for each patient as related to the identified diseases or adverse events. In blocks 92 and 94, one or more lists showing those patients with the highest risks for each identified disease or adverse event are generated, transmitted, and otherwise presented to designated medical staff, such as members of an intervention coordination team. These lists may be populated in real-time, or otherwise regularly according to a recurring schedule depending on hospital capability and resources. The intervention coordination team may then prescribe and follow targeted intervention and treatment plans for inpatient and outpatient care. In block 96, those patients identified as high-risk are continually monitored while they are undergoing inpatient and outpatient care. The method 80 ends in block 98.

Not shown explicitly in FIG. 6 is the de-identification process, in which the data become disassociated with the patient's identity to comply with HIPAA regulations. The data can be de-coupled with the patient's identity whenever they are transmitted over wired or wireless network links that may be compromised, and otherwise required by HIPAA. The method 80 is further adapted to reunite the patient data with the patient's identity.

Figure 7:
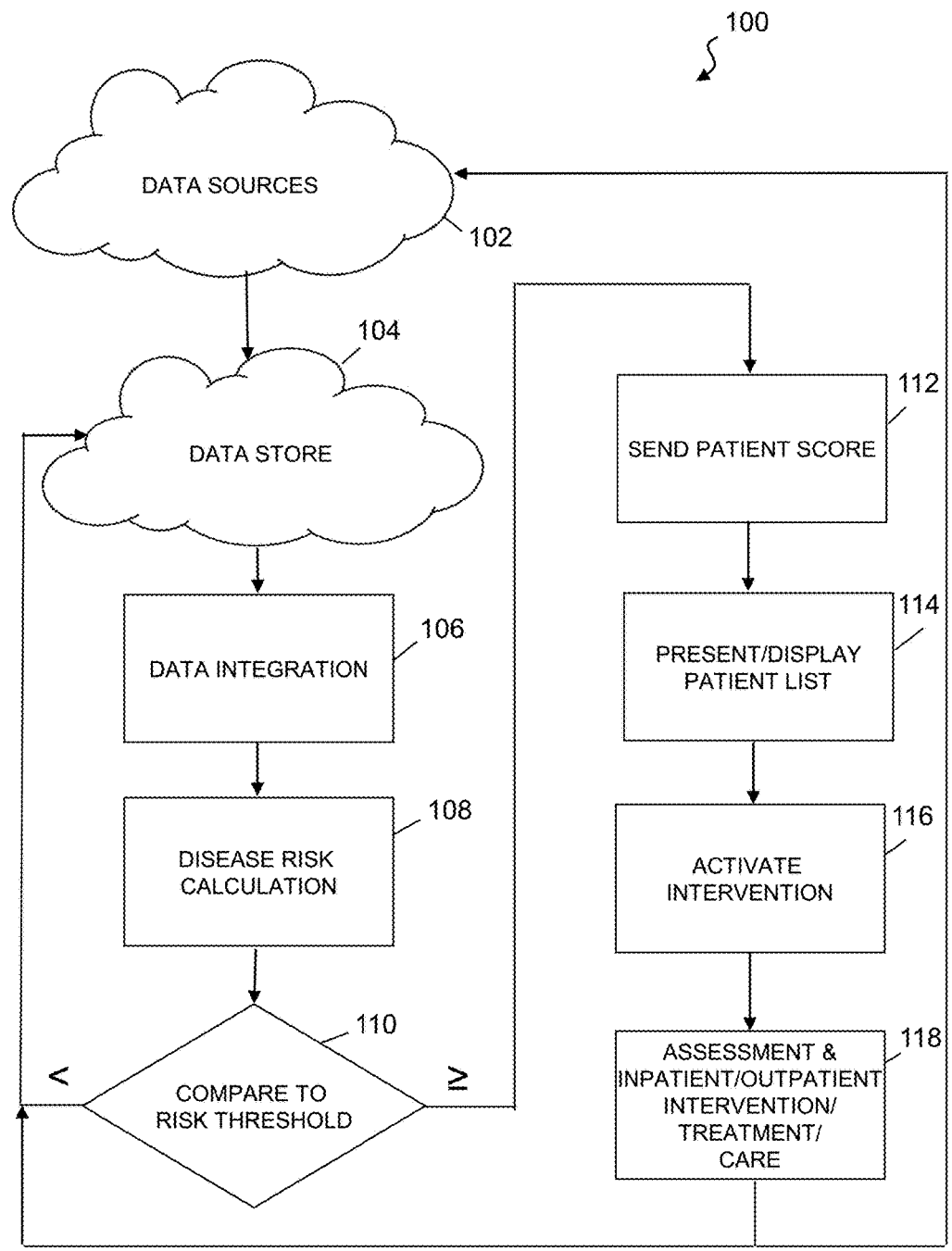
FIG. 7 is a simplified flowchart/block diagram of an exemplary embodiment of a clinical predictive modeling method, describing the application of predictive analytics across the different stages of a patient's clinical encounter in various settings of care, according to the present disclosure.

FIG. 7 is a simplified flowchart/block diagram of an exemplary embodiment of a clinical predictive modeling method 100 according to the present disclosure. A variety of data are received from a number of disparate data sources 102 related to particular patients admitted at a hospital or a healthcare facility. The incoming data may be received in real-time or the data may be pulled in batches. The incoming data are stored in a data store 104. In block 106, the received data undergo a data processing and integration process following data extraction (e.g., data cleansing and data manipulation), as described above. The resultant data then undergo the disease risk logic process 108 during which disease identification, and predictive modeling are performed. The risk score (with specific regard to high risk) computed for each patient for a disease of interest is compared to a disease high risk threshold in block 110. Each disease is associated with its own high risk threshold. If the risk score is less than the high risk threshold, then the process determines if the patient's risk score falls into the medium or low risk categories, otherwise the process returns to data integration and is repeated when new data associated with a patient become available. If the risk score is greater than or equal to the high risk threshold, then the identified patient having the high risk score is identified as 'high risk' and included in a patient list in block 112. In block 114, the patient list and other associated information may then be presented to the intervention coordination team in one or more possible ways, such as transmission to and display on a desktop or mobile device in the form of a text message, e-mail message, web page, etc. In this manner, an intervention coordination team is notified and activated to target the patients identified in the patient list for assessment, and inpatient and outpatient treatment and care, as shown in block 118. The process may thereafter provide feedback data to the data sources 102 and/or return to data integration 106 that continues to monitor the patient during his/her targeted inpatient and outpatient intervention and treatment. Data related to the patient generated during the inpatient and outpatient care, such as prescribed medicines and further laboratory results, radiological images, etc. may be continually monitored to track intervention completion.

Figure 8:
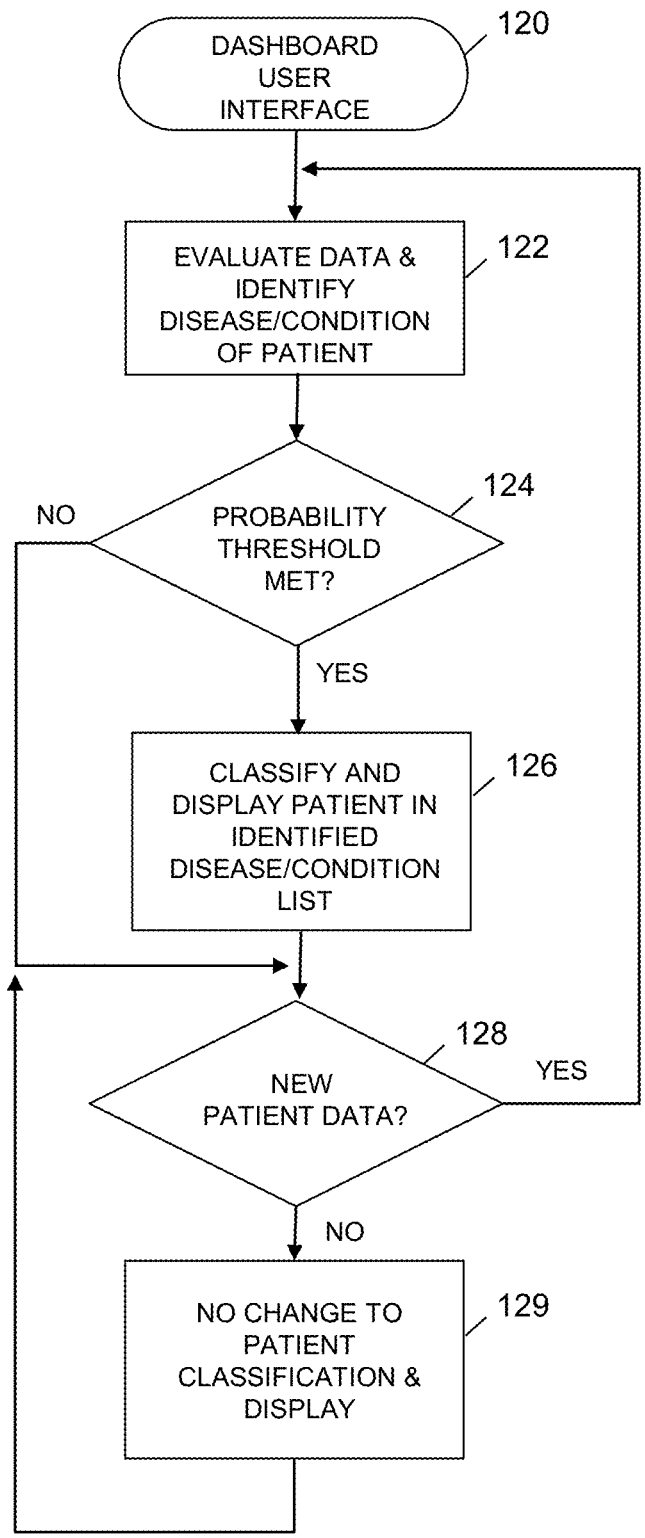
FIG. 8 is a simplified flowchart diagram of an exemplary embodiment of a dashboard user interface method according to the present disclosure.

FIG. 8 is a simplified flowchart diagram of an exemplary embodiment of a dashboard user interface method 120 according to the present disclosure. The patients' data are evaluated as described above, and those patients associated with targeted diseases and surveillance conditions are identified in block 122. The targeted diseases are those illnesses that the patient is at risk for readmission to the healthcare facility. The monitored conditions are those patient conditions, e.g., injury and harm, that are indicative of occurrence of adverse events in the healthcare facility. The patients' inclusion on a particular disease or surveillance condition list is further verified by comparison to a predetermined probability threshold, as shown in block 124. If the probability threshold is met, then the patient is classified or identified as belonging to a disease list or condition list. The display is also updated so that when a user selects a particular disease list for display, that patient is shown in the list, as shown in block 126. In this exemplary screen, the list of patients that are at risk for 30-day readmission due to congestive heart failure (CHF) are identified and listed in the active congestive heart failure list. Details of the exemplary screen are provided below.

The user may use the displayed information acknowledging and adhering to patient privacy protocols, and generate standard or custom reports. The reports may be primarily textual in nature, or include graphical information. For example, a graphical report may chart the comparison of expected to observed readmission rates for any disease type, condition, or category for patients enrolled or not enrolled in an intensive intervention program, the readmission rates for enrolled versus dropped patients over a period of time for any disease type, condition, or category. Patients with greater than 95%, for example, probability of having heart failure, total versus enrolled in an intervention program over a specified time period, and the number of patients not readmitted within 30-day discharge readmission window. Additional exemplary standard tracking reports that may further identify all enrolled patients for which: post-discharge appointments are scheduled, post-discharge phone consults are scheduled, patient has attended follow-up appointment, patient has received post-discharge phone consult, patient has received and filled medical prescriptions, and patient has received transportation voucher. Further sample reports may include a comparison of expected to observed readmission rates for any disease type, adverse event, or category for intervention program-enrolled and not enrolled patients, or readmission rates for intervention-enrolled vs. dropped patients over a period of time for any disease type, adverse event, or category. Another type of report available is outcome optimization reports. These are reports designed to help users (administrators) assess the benefit and efficacy of a program, establish benchmarks, and identify needs for change on systematic and population levels to improve care outcomes. The report may include data that assist in assessing the effectiveness of the identifying high risk patients. Some of the data may demonstrate effort spent, patients enrolled in an intervention program following designation as high risk for an adverse event, and how often those patents truly are afflicted with the identified diseases. Reports may include data that assist in assessing whether interventions are given to the right patients, at the right time, etc.

As new, updated, or additional patient data become available, as shown in block 128, the data is evaluated to identify or verify disease/condition. The patient may be reclassified if the data now indicate the patient should be classified differently, for example. A patient may also be identified as potentially being diagnosed with an additional disease and be classified as such. For example, in the first 24 hours of admissions, the system identifies a particular patient as having CHF. Upon receiving more information, such as lab results and new physician notes, the system identifies this patient as also having AMI. Thus, this patient is identified as an AMI candidate and a CHF candidate.

If there are no new patient data available or accessible to the disease component/risk logic modules, then there is no change to the patient classification and the display reflects the current state of patient classification, as shown in block 129. Accordingly, as real-time or near real-time patient data become available, the patients' disease and adverse event classifications are re-evaluated and updated as necessary.

Targeted predictive readmission diseases may include: congestive heart failure, pneumonia, acute myocardial infarction, diabetes, cirrhosis, and all cause. Targeted disease or adverse event identification may include: sepsis, chronic kidney disease, and diabetes mellitus. Targeted conditions due to a possible adverse event for surveillance may include: sepsis, post-operative pulmonary embolism (PE) or deep vein thrombosis (DVT), post-operative sepsis, post-operative shock, unplanned return to surgery, respiratory failure, hypertension, unexpected injury, inadequate communication, omission or errors in assessment, diagnosis, or monitoring, falls, hospital-acquired infections, medication-wrong patient, patent identification issues, out-of-ICU cardiopulmonary arrest and mortality, chronic kidney disease, shock, trigger for narcan, trigger for narcotic (over-sedation), trigger for hypoglycemia, and unexpected death.

The evaluation may include users inputting observations and comments about the patient, for example. As a part of the evaluation process, a user (a healthcare provider) may confirm, deny, or express uncertainty about a patient's disease or adverse event identification or intervention program enrollment eligibility. For example, the user may review, via the user interface, notes and recommendations associated with a particular patient and confirm the inclusion of that patient in the congestive heart failure list for intervention program enrollment, as shown in block 108. The user may review the clipped clinician's notes that call attention to key words and phrases that led to a disease identification by the system. Key terms such as "shortness of breath," "BNP was elevated," and "Lasix" may help the user validate the disease identification of CHF for that patient, and validate enrollment of the patient into a specific intervention program. If the patient's classification, risk level, and eligibility level are confirmed, there is no change in the patient's classification and the data that are displayed (except to indicate this classification has been confirmed), as shown in block 109. The user may supply or enter comments associated with the confirmation. The user may disagree with the inclusion of the patient in the congestive heart failure list, or express uncertainty or enter comments explaining his or her assessment. User comments are stored and can be seen by other users, allowing clear and timely communication between team members. The user may proceed to select a report or a display parameter, or review and evaluate particular selected patients.

If the user disagrees with the patient's the classification, then the patient is removed from the active list of the target disease or condition, and placed on a drop list. In response to the user denying the classification, the system may additionally display or flag information about the patient that contributed to the inclusion of the patient on a particular list. For example, if the user denies the disease identification that John Smith has heart failure, the system may further request confirmation wherein which the user is required to respond to the query with yes or no. The system may additionally request rationale from the user for wanting to remove the patient from the active list. The rationale supplied by the user may be stored and displayed as reviewer comments. The user may also indicate uncertainty, which may result in the patient being removed from the active list and placed on a watch list for further evaluation. The user may then review and evaluate additional patients on the same target disease list or review patients included on other disease and adverse event lists. At any point, the user may use, with compliance and adherence to patient privacy protocols, in some form, the displayed information, such as generating standard or custom reports.

As an example, a patient is identified as a CHF patient at the time of admission. After receiving more data (i.e., new lab results and new physician notes) during her hospital stay, the system has identified this patient as having AMI.

The clinician notes upon admission states: 52 yo female w pmh of CAD, also with HTN presents with progressively worsening SOB and edema 1 month. 1. Dyspnea: likely CHF with elevated BNP afterload reduction with aCEi and diuresis with Lasix. O2 stats stable 2) elevated troponin: EKG with strain pattern follow serial enzymes to ROMI and cards consulted for possible Cath. The clinician notes thereafter states: 52 yo female with pmh of CAD, also with HTN presents with progressively worsening SOB and edema 1 month c CAD with LHC with stent prox LAD. 1. Elevated troponins—NSTEMI, despite pt denying CP—pt with known hx of CAD, mild troponin leak 0.13→0.15→0.09→0.1—on admission pt given 325, Plavix load with 300 mg 1, and heparin gtt—Metop increased 50 mg q6, possibly change Coreg at later time—LHC today per Cardiology, with PCI. also discuss with EP for possible ICD placement 2. Heart failure, acute on chronic—severe diastolic dysfunction be due HTN off meds+/–CAD—proBNP elevated 3183 on admission—initially started on lasix 40 tid, edema much improved, now on lasix 40 po bid—TTE completed showing: 4 chamber dilatation, RVH, nml LV thickness, severely depressed LVSF, LVEF 30%, mod MR, mild TR, AR and PR; severe diastolic dysfunction, RVSP 52—continue on Lasix, Lisinopril, Metop—discuss AICD evaluation with EP vs initial medical management.

The reviewer may assess the above admission notes with the disease identification of CHF compared with a disease identification of AMI by the system 10 in an effort to validate this new real-time disease identification. The admission note indicated CHF as the primary disease. Key highlighted terms that are indicative of CHF include "pmh of CAD" (past medical history of coronary artery disease, "SOB" (shortness of breath), "edema," "elevated BNP." The second note indicates that while the patient has CHF, CAD is the primary cause of the CHF. Key highlighted terms such as "elevated troponins" and "NSTEMI" (Non ST Segment Myocardial Infarction: heart attack) give the reviewer a snapshot view of the key terms the system used to identify AMI as the primary disease. These highlighted key terms give the reviewer the tools to validate in real-time or near real-time the system's recommended change in disease identification. The reviewer can then confirm, deny, or express uncertainty with the new disease identification, and note any validation or rejection in his or her personal notes. In any scenario, the system will provide likely disease diagnosis based on data inputs, but can be overruled by the expert opinion of a physician reviewer. Because the patient's primary recommended intervention pathway would be for AMI, the patient, corresponding disease identification, and risk level would appear in the AMI list.

The dashboard user interface 75 may also indicate a change in the level of risk. For example, upon return of recent lab results (e.g., slightly elevated creatinine and tox screen positive for cocaine) and other (updated) social factors that influence risk (e.g., noncompliance with sodium restriction due to homelessness) as well as medical pathway language queues, and prior admission history, the system may identify a patient initially evaluated to be at medium risk of readmission to currently be at high risk for readmission. A reviewer can follow these changes in real-time and to validate the change in risk level and take any additional appropriate action.

The holistic hospital patient care and management system and method 10 further include a number of novel features shown in FIGS. 9-16 described below.

Figure 9:
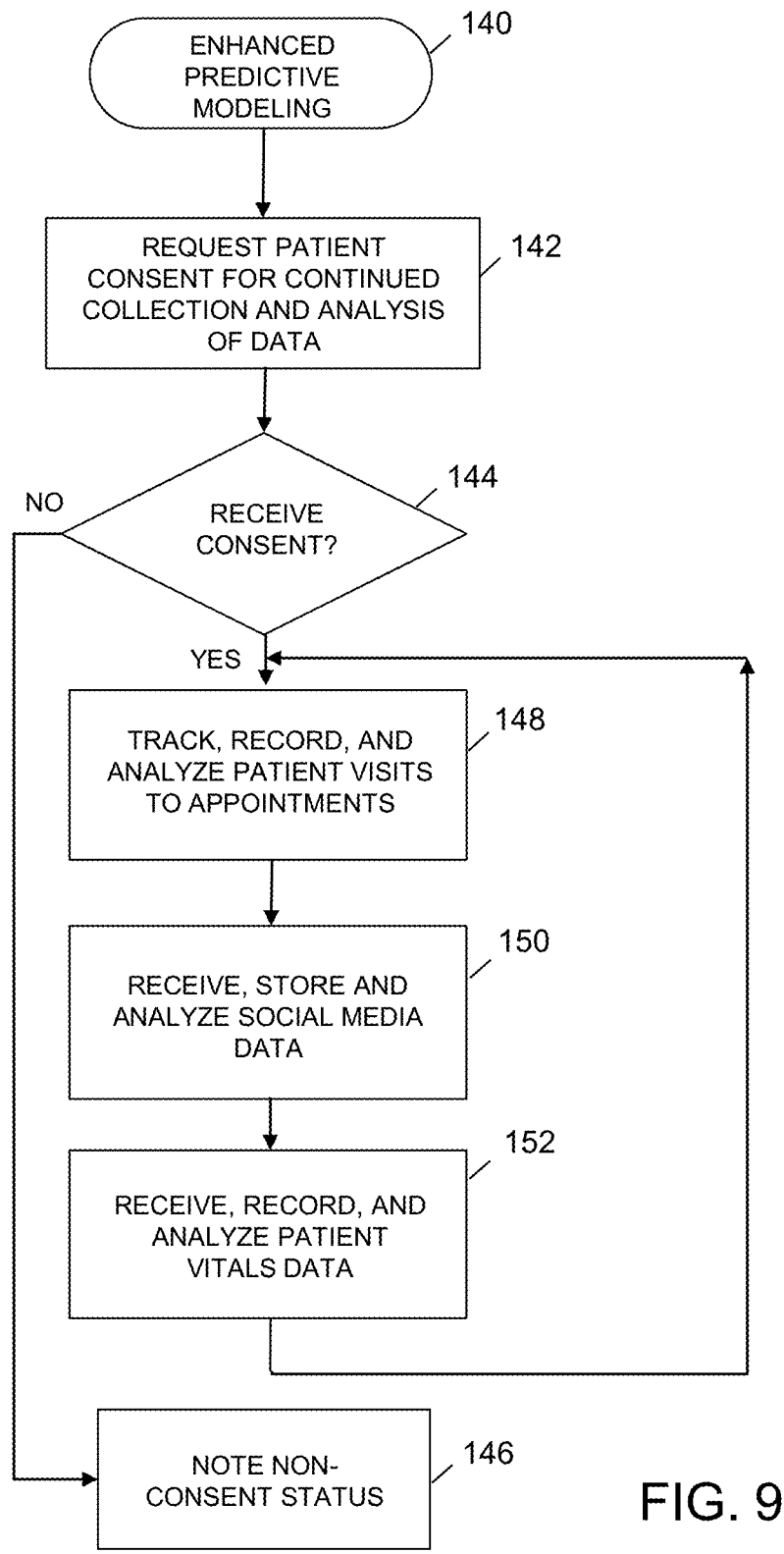
FIG. 9 is a simplified flowchart of an exemplary embodiment of an enhanced predictive modeling method according to the present disclosure.

FIG. 9 is a simplified flowchart of an exemplary embodiment of an enhanced predictive modeling method 140 according to the present disclosure. In block 142, the patient's consent for continued collection and analysis of the patient's data is requested. Because the enhanced method will continue to track and monitor the patient's wellbeing and collect data associated with the patient for analysis, the patient's consent is sought to comply with all local, state, and federal regulations. If the patient's consent is not received or the patient declined, as determined in block 144, then the patient's no consent status is recorded in the system's database, as shown in block 146. If the consent is received in block 144, then the patient's visits to clinical/medical and non-medical/social service appointments are monitored and tracked and data recorded, as shown in block 148. This may be done automatically, such as tracking the patient's location using, for example, RFID, WiFi, or GPS methods. Alternatively, data received or taken at each visit to these scheduled or unscheduled appointments are recorded in the system for analysis. The patient's social media data may also be received and stored for analysis, upon receipt of patient consent, as shown in block 150. With regard to tracking clinical variables post-discharge, the patient's vitals may be continuously monitored and taken automatically or otherwise for analysis, as shown in block 152 through an electronic device (worn by the patient) that is capable of measuring the vitals of the patient on a periodic basis, such as once or twice a day. This information may be automatically relayed or transmitted to the system 10 directly or via a portal or information exchange. The enhanced predictive model is capable of serving as a reliable warning tool for the timely detection and prevention of adverse events. Its functionality may include patient risk stratification, notification of clinical staff of an adverse event, and identification of health service and relevant social service organizations based on the patient's location to best serve the patient's needs. The system 10 may notify caregiver or healthcare provider via, for example, pages, best practice alerts, conventional alerts, and visualization reports.

Figure 10:
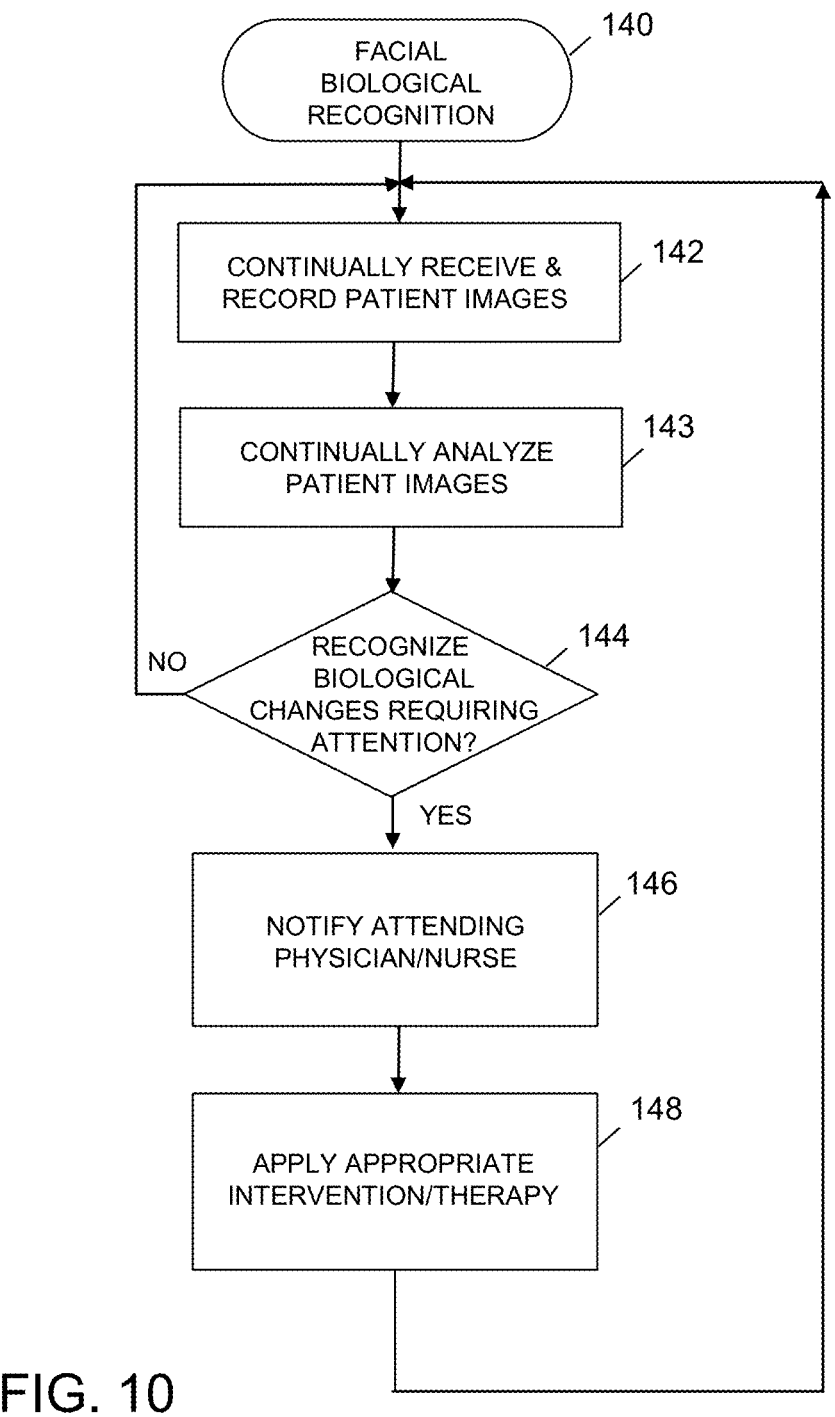
FIG. 10 is a simplified flowchart of an exemplary embodiment of a facial and biological recognition process according to the present disclosure.

FIG. 10 is a simplified flowchart of an exemplary embodiment of a facial and biological recognition process 140 according to the present disclosure. It is assumed that the patient has given all required consent for the enrollment into this program. One or more video and/or still cameras are placed in strategic locations in the patient's room. For example, a camera may be mounted on the ceiling above the patient's bed to be able to capture unimpeded visible light and infrared thermal images of the patient's face. In addition, nurses attending to the patient may wear a video camera attached to his uniform, glasses, or other accessories. The cameras are preferably capable of capturing high definition and high quality images. These images may be accessible by attending physicians and nurses. In block 142, the system continually receives images of the patient, and records those images. In block 143, the system continually analyzes the patient's images to detect biological changes indicative of an adverse clinical outcome which may not have physically manifested in the patient yet. The algorithm considers abnormalities in variables such as body temperature, conjunctival color, pupillary responsiveness, facial expression, etc. The system uses facial recognition and artificial intelligence software to recognize and detect certain changes in temperature, color, and expressions. For example, a change in the patient's conjunctival color may be identified as a possibility that the patient is becoming anemic due to anostomotic hemorrhage post-surgery. A mild change in the patient's pupillary responsiveness may be detected by the system as a change in intra-cranial pressure that requires attention. The system may also recognize an expression on the patient's face that indicates the patient is experiencing pain or severe discomfort.

In block 144, these biological changes in the patient are recognizes as requiring prompt attention by caregivers. In block 146, the attending physician and/or nurse is notified or alerted. These alerts may be sent, for example, via page, text message, call, or the PB system, and may be preferences set by the individual caregivers. In block 148, prompt attention and appropriate intervention and therapy can then be ordered by the healthcare providers to timely address the issue(s) that brought on the detected biological change.

Figure 11:
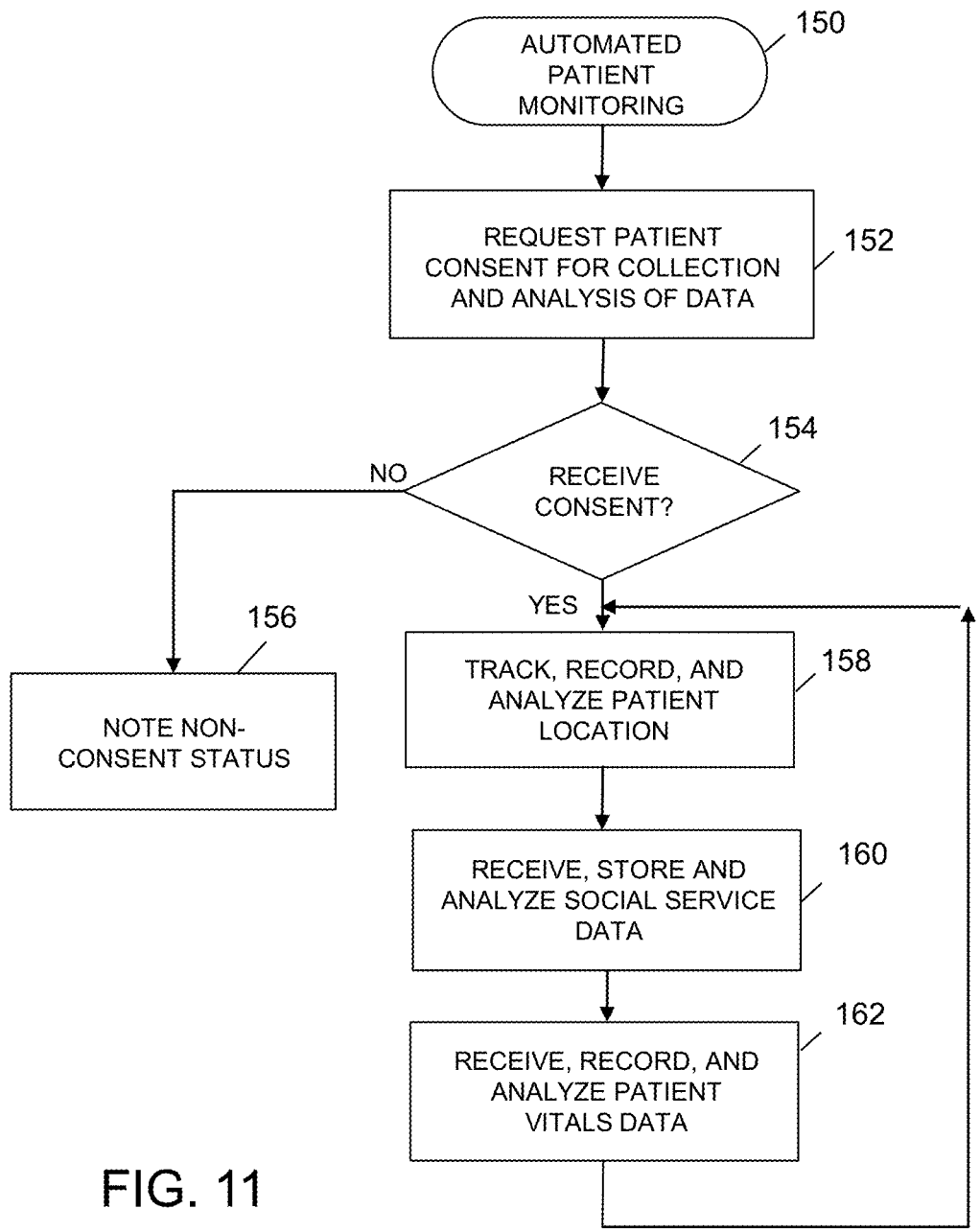
FIG. 11 is a simplified flowchart of an exemplary embodiment of an automated patient monitoring process according to the present disclosure.

FIG. 11 is a simplified flowchart of an exemplary embodiment of an automated patient monitoring process 150 according to the present disclosure. In block 152, the patient's consent for the collection and analysis of data is requested. If the patient does not give consent, as determined in block 154, then the patient's no consent status is noted in the system in block 156, and the patient is not enrolled in this program. If the patient does provide consent, then the patient is tracked and monitored in a number of ways, including location, social service appointments and visits, and vitals, as shown in blocks 158-162.

The patient's location may be determined using various suitable technologies, including RFID, GPS, and WiFi/cell tower triangulation. The patient may be given an RFID bracelet or another form of accessory when the patient was first admitted in a hospital. The patient's location may then be tracked by a plurality of RFID sensors distributed within the hospital. In addition, clinical and social service organizations that participate in this patient monitoring program may be outfitted with RFID so that when the patient visits the organization for an appointment, his presence is detected. As mobile devices such as mobile telephones equipped with GPS capabilities has become ubiquitous, a patient's location and movement may also be tracked using the device's GPS functionality and relayed back to the system via an application (app) downloaded to the patient's device. The sensors and mobile devices are configured to transmit the patient's detected location to the system for recording and analysis. The system is able to determine that the patient's location matches up with the patient's calendar appointments for healthcare and social services, and is thus properly following prescribed therapies and treatment. This functionality combined with disease and risk identification functions provide a capability of identifying the highest priority patients based on severity of disease and deploying the right resources to the most vulnerable patients in timely manner. Patients that repeatedly fail to follow prescribed therapies may cause an alert to be generated and sent to healthcare providers or social service providers so that additional, more focused assistance or guidance may be given to the patient.

Figure 12:
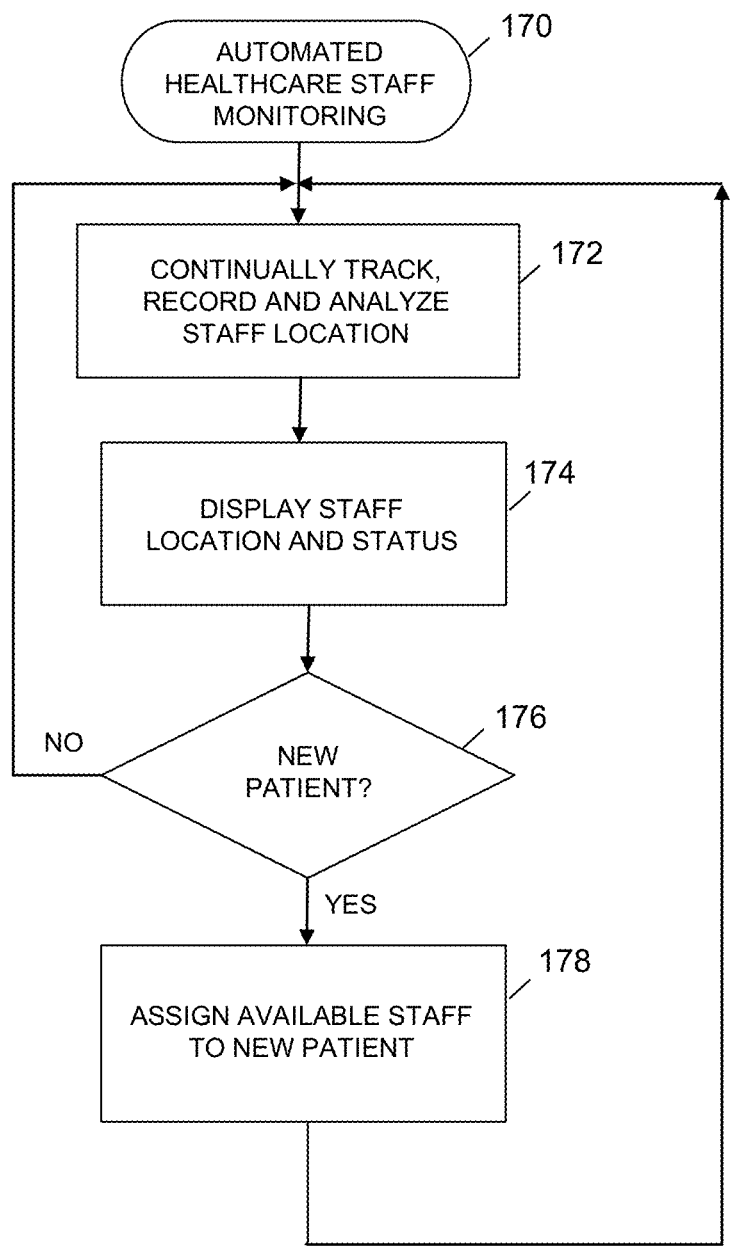
FIG. 12 is a simplified flowchart of an exemplary embodiment of an automated healthcare staff monitoring process according to the present disclosure.

FIG. 12 is a simplified flowchart of an exemplary embodiment of an automated healthcare staff monitoring process 170 according to the present disclosure. This function is capable of assessing existing nurse availability and workload and producing new staff assignments based on current or expected patient inflow. Healthcare staff such as nurses are given ID badges that have embedded RFID tags that respond to RFID sensors distributed throughout the hospital facility. In block 172, using RFID technology, each nurse's location can be determined, tracked, and recorded. As part of the analysis, a nurse that is inside a patient's room or substantially co-located with a patient is automatically identified as "busy" or "with patient." The system may also receive input from the nurses who can manually indicate on a user interface (of software application executing on a computing device such as mobile telephone, laptop computer, and desktop computer) or in some other manner that they are "busy" or "available." The nursing staff for each department may be clearly marked or delineated along with the patients assigned to each nurse. The system continually receives the nursing staff's location information and makes a determination on whether each nurse is "busy" or "available." The nursing staff location and status are displayed on a graphical user interface of the system, as shown in block 174. The nurses' location, current (real-time) status, and department designation are presented via the graphical user interface at one glance.

When a new patient arrives or is admitted, as determined in block 176, the status and location of each nurse working that shift for a particular department can be clearly viewed on the user interface. In block 178, an available nurse may be selected and assigned to the new patient, an alert or message is sent to the nurse to inform him/her of this new assignment, and the nurse's status is immediately updated in the system. A nurse or another healthcare staff may also be notified in advance of anticipated need via this function. For example, one or more emergency department nurses that are currently "available" may be selected to receive notification that seven critically injured patients from a multi-car accident are in transit to the hospital with the estimated arrival time. In this manner, RFID technology is used to monitor and track the nursing staff at any given moment in order to identify available human resources on a real-time basis that are capable to offering care to incoming patients. Thus, human resources may be efficiently assigned and utilized.

Figure 13:
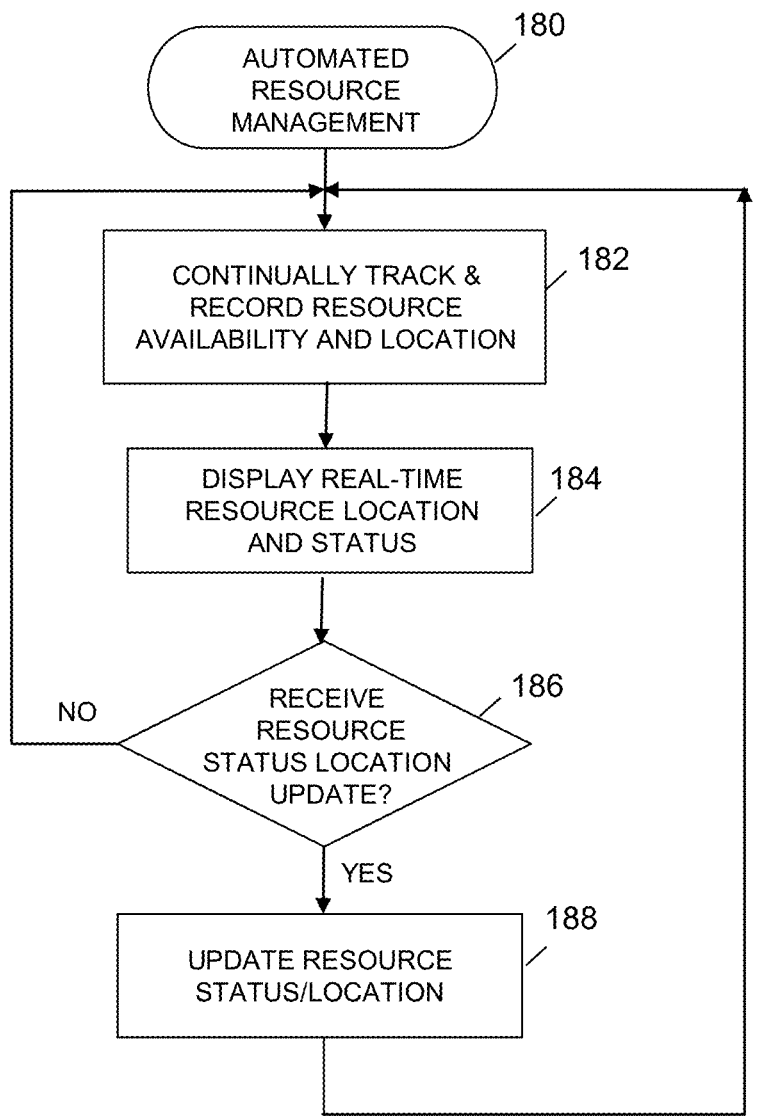
FIG. 13 is a simplified flowchart of an exemplary embodiment of an automated resource management process according to the present disclosure.

FIG. 13 is a simplified flowchart of an exemplary embodiment of an automated resource management process 180 according to the present disclosure. This function is capable of tracking/monitoring hospital resource availability, deficiencies, and surpluses. Further, this function may be used to reserve resources for anticipated use. For example, the system may be used to hold a hospital bed for a patient undergoing testing; 2) notify appropriate staff to turnover beds for patients who have been discharged/transferred; and 3) indicate free beds once necessary cleaning and maintenance has occurred following patient discharge/transfer. The system may be used to track and monitor all resources in a hospital, including patient beds, medical equipment, medicine, and supplies. All of these resources have an RFID tag that communicates with RFID sensors distributed throughout the hospital. For example, the system can detect and determine that certain equipment and supplies are located in a specific storage room and/or in a particular storage cabinet. Further, if a patient's RFID tag is co-located with the RFID tag of a particular hospital bed, then the system determines that the patient is occupying that bed and that bed is not available.

In block 182, the system receives RFID sensor output that informs the system of the location of each resource item. This information is recorded and analyzed. The resource information is also presented or displayed via a graphical user interface that provides an at-a-glance view of which bed (hospital room) is available for incoming patients, what equipment and supplies are available, as shown in block 184. When a status change is indicated, either automatically detected (e.g., when an item is moved as detected by RFID sensors) or by user input (e.g., when an assignment to a patient is entered by a user), the item's status is updated in the system, as shown in block 188. For example, a nurse may use a handheld barcode scanner to scan supplies and drugs that are being readied and used for a particular patient. The information from the scan would then be transmitted to the system, which would update the status and location of these items in the appropriate inventory tracking module. As another example, a nurse may scan, via the graphical user interface, that four emergency beds should be reserved as four critical patients are being transported to the hospital from an industrial accident. This information would be sent back to the system, and the quantity of required beds would be held by notification status of HOLD next to the unit/room number in the bed listing for the hospital. The process returns to block 182 to continually monitor and update resource location and status.

Figure 14:
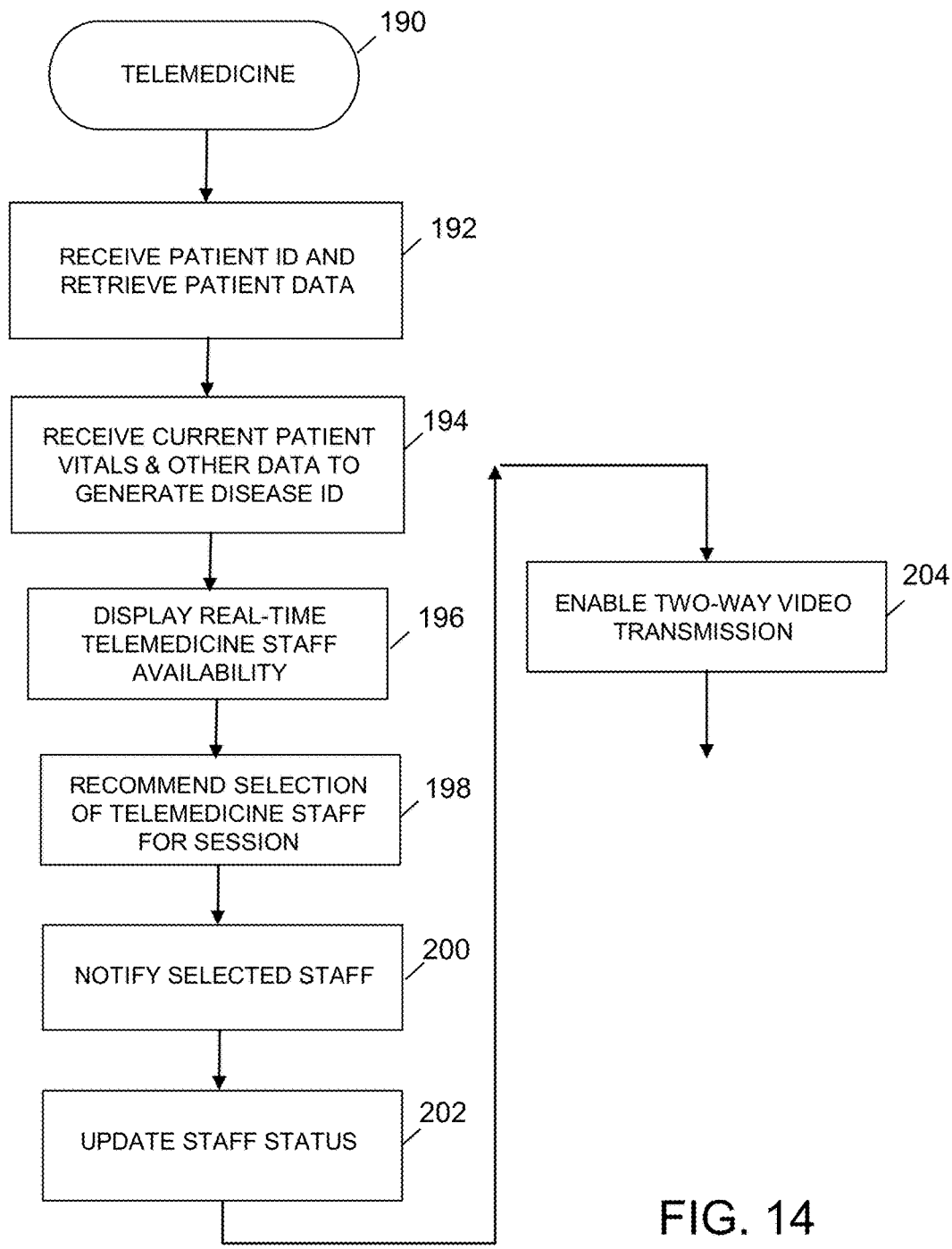
FIG. 14 is a simplified flowchart of an exemplary embodiment of a telemedicine process according to the present disclosure.

FIG. 14 is a simplified flowchart of an exemplary embodiment of a telemedicine process 190 according to the present disclosure. The telemedicine function is configured to resolve the issue of competing and high priority demands faced by clinical staff. Functionality includes the identification of physicians who are able to provide remote clinical assessments and validate disease identification. Scenarios in which telemedicine is initiated are when the patient is taken to a clinic where specialized medical staff is not available for consult for the patient's disease or condition. Alternatively, a telemedicine session may be initiated when paramedics are assisting a patient and they need immediate assistance or consultation with a physician to deal with a time sensitive condition. In block 192, the patient's name and/or other forms of identifier is entered by the attending personnel assisting the patient. Using the patient's identification information, the patient's clinical and non-clinical data are retrieved from the data store, and displayed if necessary. The patient's current vitals and other information taken by the attending personnel are entered into the system and recorded, as shown in block 194. The patient's medical history along with the current vitals and other information are used by the predictive model to identify a disease. This information is used to select a physician or other telemedicine staff that are available for the present telemedicine session. The physicians' medical specialties are considered for the selection. In block 196, the available physicians and staff are displayed by specialty area. A selection may be recommended by the system taking all data into account or received by a manual selection by the attending personnel, as shown in block 198. In block 200, the selected physician or staff is alerted or notified by a method preferred by that person. The status of the selected physician or staff is updated, as shown in block 202. In block 204, a two-way encrypted video session between the telemedicine physician and the attending personnel is initiated to enable the two parties to communicate, view the patient, share notes, and attend to the patient. In this manner, the best qualified telemedicine physician available may be automatically selected or recommended by the system to be consulted for the care of the patient.

Figure 15:
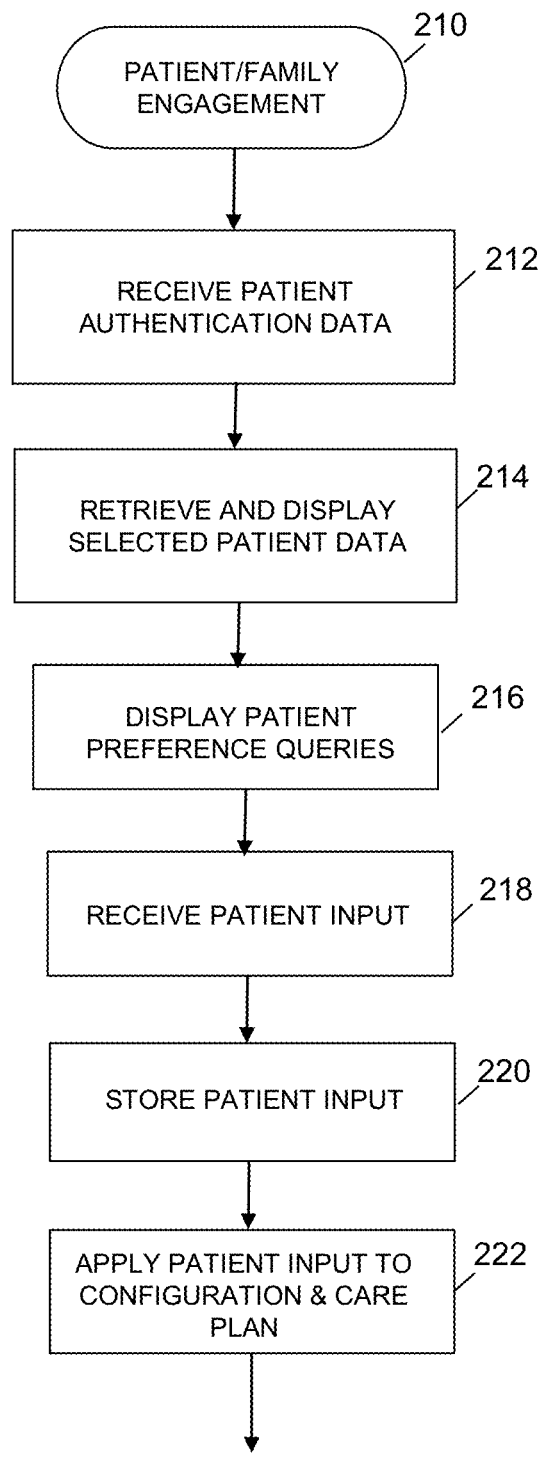
FIG. 15 is a simplified flowchart of an exemplary embodiment of a patient/family engagement process according to the present disclosure.

FIG. 15 is a simplified flowchart of an exemplary embodiment of a patient/family engagement process 210 according to the present disclosure. This function is capable of serving as a repository of reference material to inform provider decision-making and assist patients/families in self-care and disease management. This function further allows patients to describe all medical issues and submit questions to ensure that physician-patient communication is as efficient and transparent as possible. A patient's family is also provided with opportunities to be notified of patient status in an effort to increase awareness and shared decision-making during complicated situations, such as surgery. A software application may be provided to the patient or the patient may download the app to a computing device, such as a mobile device or laptop computer. The patient and family member may be provided access to this function at admission to the hospital, with it remaining accessible even after discharge from the hospital, contingent on adequate Internet accessibility. In block 212, the patient and/or family member that have been given access to this function may enter authentication data or login information. Once the access is authenticated, a selective subset of the patient's data are retrieved from the data store and displayed, as shown in block 214. Also displayed are resources available to the patient, such as information related to a particular disease that the patient is being treated for, information related to a therapy or treatment that the patient is undergoing, information about available support groups, etc. The system further displays queries that solicit the patient's and family's preferences, as shown in block 216. The patient and family members may provide their preferences by inputting them or selecting from among available options, as shown in block 218. For example, the patient or family member may indicate the preferred rounding time, preferred family notification method, privacy preferences for communication, and online health history. The received input are stored and made available to healthcare workers and social service workers, where necessary, and are applied to modify the system configuration (e.g., how the system notifies patient or family) and the patient's care plan where suitable, as shown in block 222.

Figure 16:
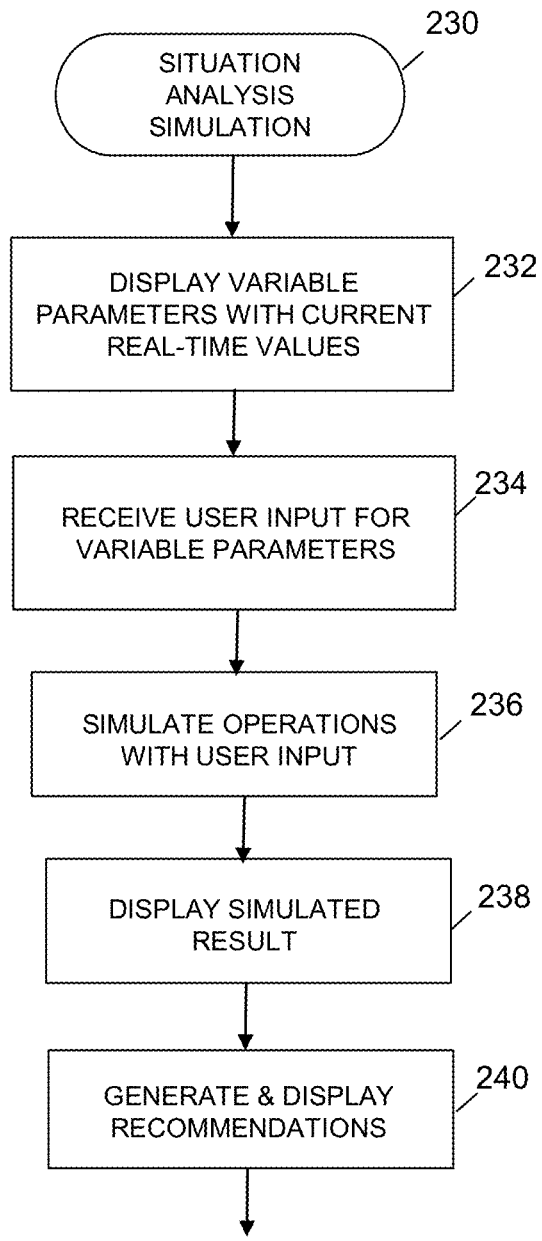
FIG. 16 is a simplified flowchart of an exemplary embodiment of a situation analysis simulation process according to the present disclosure.

FIG. 16 is a simplified flowchart of an exemplary embodiment of a situation analysis simulation process 230 according to the present disclosure. This function gives the hospital administrator the ability to simulate 'what-if' scenarios by adjusting different parameters and observing the expected impact on operations will facilitate appropriate planning to optimize existing resources, thereby enhancing operational efficiency. The use of real-time data used to run the simulations will provide reasonable confidence in the application of simulated results to current and future resource planning In block 232, the method displays input parameters that can be varied to simulate certain scenarios. The parameters may include the number of available beds, the number of patients, then number of physicians, the number of nurses, the number of certain medical equipment, the amount of certain medical supplies, etc. In block 234, the user is provided the ability to alter or change these parameter values to see what would happen to the operations of the hospital. For example, the user may increase the number of patients needing care in the emergency department by two fold due to a multi-car accident. The user may reduce the number of available beds and decrease the number of physicians available to tend to the patients due to a high patient volume day. The user may lower the number of physicians, and increase the number of nurses available due to more severe cases (e.g., surgeries) requiring physician (rather than nurse) supervision. The user may indicate the time period of the simulation in terms of days, weeks, months, for example. The system receives the user input, as shown in block 234, and uses the predictive model to simulate the scenario described by the user input in block 236 in order to evaluate options based on potential financial, operational, or clinical outcomes (as selected by the user) as demonstrated by the simulation. The system has access to current real-time data about patient status, healthcare staff availability, resource and supply availability, and other information that are modified or influenced by the user simulation input. The system may identify and display if, when, where, and how patient care would be compromised with the simulation input, as shown in block 238. The system may further identify recommended actions or advanced precautions that can be taken to address shortcomings identified in the simulation, as shown in block 240.

For example, in the case of simulating a large influx of new emergency department patients, the system may identify one or more patients who are currently occupying beds in the emergency department who can be safely discharged or moved to other departments of the hospital without compromising their care and treatment. These are patients who have been determined by the predictive model to be at low risk for adverse events (e.g., readmission) for example. In this manner, hospital administrators and physicians may make advanced informed decisions about staffing mix, adjusting resources and supplies, and inpatient care to achieve better efficiencies and outcomes.

A number of use cases are described below to further illustrate the operations of the holistic hospital patient care and management system and method 10.

Use Case 1—Cardiology Surgery

Time-to-surgical repair is an important factor determining outcomes for patients identified to be at high-risk of having a ruptured abdominal aortic aneurysm (AAA). As such, there is great value and significance derived from a highly sensitive and specific predictive model capable of risk stratifying patients with potential AAA rupture due to the typically asymptomatic nature of this condition. Specifically, the U.S. Preventive Services Task Force (USPSTF) has issued a recommendation for men between the ages of 65 and 75 with a history of smoking to be screened for AAA due to the common absence of symptoms for this condition, and the high potential for adverse outcomes if AAA rupture is left untreated.

In this example, the patient is a 68 year-old male who arrives at the emergency department complaining of back pain and is found to have hypertension. The predictive model detects that this patient is at high risk of having a ruptured AAA, and transmits an alert to the physicians, appropriate clinical staff, and blood bank. The patient is rushed to the CT scanner, where the CT A/P confirms an AAA with partially contained internal bleeding. The patient is taken to the operating room. During surgery the patient's core temperature drops. In response, the system 10 automatically alerts the attending healthcare staff to deploy a warming device to raise the patient's body temperature, as well as adjust the operating room temperature and humidity settings.

The patient is placed on a ventilator after the surgery is completed. Four hours after leaving the operating room, while still on the ventilator, an alert is fired based on the patient's conjunctival pallor. The bedside nurse was wearing GOOGLE Glasses equipped with a video camera, which transmits the patient's image to the system 10. The system's facial recognition software and other algorithms identified that the patient was likely becoming more anemic based on change in conjunctival color. The nurse receives the alert, and calls the attending surgeon and the patient is rushed back to the operating room to control the patient's anostomotic hemorrhage. The patient then recovers from surgery and is discharged from the hospital.

Cardiology and surgical services are two areas of medicine that can be aided by innovative tools to risk stratify patients in real-time to notify the healthcare providers that individuals at high risk for developing a specific disease or condition, such as AAA rupture. These areas of medicine are highly susceptible to a wide range of adverse outcomes, such as readmissions and healthcare-associated infections (HAIs), two adverse clinical outcomes hospitals are eager to address and remedy. The system 10 can both accurately identify patients at high-risk of AAA rupture in real-time contributes to decreasing delays in administering/activating evidence-based therapies/interventions aimed at reducing the likelihood of poor outcomes due to an unintended or undetected AAA rupture.

As a result of having a reliable warning tool using the predictive model, patients with risk factors for AAA rupture, for example, can be treated in a timely manner by the appropriate clinical treatment team to avoid serious and potentially life-threatening adverse clinical outcomes, thereby improving population health and costs (through the avoidance of unnecessary utilization costs). Further, accurate risk stratification enables efficient resource/staff allocation in order to ensure that patients requiring immediate attention receive prompt attention and care.

Use Case 2—Emergency Department

Between 2003 and 2009, the mean wait time in U.S. emergency departments increased 25%, from 46.5 minutes to 58.1 minutes. It has been noted that as emergency department wait time increases, patient satisfaction declines. A common response (as a result of patient dissatisfaction at longer than anticipated wait times) is the patient leaving and going to an alternate institution or location, either leaving before examination or leaving immediately after realizing the long wait time. Solutions for improving emergency department wait time are necessary to deliver timely care to ill patients, as well as improve staff and resource allocation in the emergency department.

In this example, a patient is a 64 year-old male who has had sudden onset of right-sided weakness. Upon observation of the weakness, the patient's wife calls an ambulance, and Emergency medical services (EMS) personnel arrive to provide assistance. The EMS paramedic examines the patient and determines that the patient likely had a stroke. The paramedic initiates a telemedicine consult with a neurologist who is available at a hospital. The neurologist is able to receive needed information from the paramedic about the patient, ask questions about the patient's condition, and observe the patient by viewing a streaming video of the patient. The neurologist then orders the administration of tissue plasminogen activator (TPA) based on the patient's current vitals and a thorough conversation with the patient's family regarding the risks and benefits of treatment. The patient is immediately transported to the hospital emergency department where the TPA is prepped and immediately administered. The patient is then transferred to the Neuro-ICU. In the Neuro-ICU, the patient may be monitored by the facial and biological recognition system that is able to detect a mild change in pupillary responsiveness signaling an early change in intra-cranial pressure. This information is immediately transmitted to the healthcare staff as an alert. The healthcare staff responds by taking immediate action to intubate the patient and administer treatment for increased intra-cranial pressure. Therefore, early and aggressive treatment aided by the system 10 helps this patient regain complete neurologic functioning.

The ability to communicate remotely with a trained medical professional capable of offering sound medical diagnosis and treatment advice in a timely fashion may significantly improve patient clinical outcomes, especially for conditions like stroke, where time-to-treatment significantly impacts outcomes. Further, as resources such as clinical staff face competing and high priority demands, the use of telemedicine services may reduce the number of required on-site clinical patient evaluations and assessments, providing in-house clinical staff with more time to allocate to those patients requiring in-person services. Additionally, tools such as facial recognition capable of detecting biological changes serves as warning mechanisms allowing medical professionals to act proactively to prevent adverse events and poor outcomes.

The emergency department is plagued by prominent issues such as crowding, delays, and diversions which prevent the delivery of high quality care. Telemedicine services may alleviate these burdens by increasing access to care, while potentially reducing costs associated with that care. As a result of improved care through the use of telemedicine services, the patient experience is enhanced, which as an influencer of reimbursement (HCAHPS), will likely positively impact financial payment for the hospital.

Use Case 3—Intensive Care Unit

As a result of factors such as the inherently critical and complex nature of patients who frequent the intensive care unit (ICU), as well the lack of complete information about these patients to help inform decision-making, time is a critical component contributing significantly to outcomes for patients in this specific setting of care. Furthermore, due to issues around ICU bed supply and utilization, time must be adequately factored into the care plan of every patient within this unit to ensure that the clinical status of ICU patients do not deteriorate, especially when recovery is possible. Therefore, efficient management of the finite human and non-human resources within the ICU is vital.

In this example, a bus filled with senior citizens turns over on an interstate highway. Emergency medical services (EMS) dispatch multiple ambulances to the scene to bring approximately 30 patients to the emergency department. Upon EMS dispatch, a single order is triggered that is transmitted throughout the hospital to personnel in the emergency department, operating room, ICU, and on hospital floors. As a result of the order, the following actions are carried out in each of the wards: the emergency department stops taking new patients, and clears all trauma bay for the accident victims; a patient waiting for an elective surgery in the hospital operating room has his case delayed; three patients who are flagged for discharge from the ICU are immediately given hospital beds and moved out of the ICU; and 10 patients, waiting to be discharged, are expediently given discharge orders. The system 10 automatically pages or notifies the on-call nursing staff. Current nurse workload is calculated and new nursing assignments are immediately generated to properly handle the likely surge of new patients as a result of the bus crash. Additionally, the blood bank is automatically notified to send 'O Negative' blood to the emergency department in anticipation of needed blood transfusions.

The unique nature of the ICU mandates solutions that assist an already short-staffed unit to better manage competing demands. The automated healthcare staff monitoring system which accurately communicates existing nurse availability and workload and produces new assignments based on expected patient inflow will promote better staff and resource planning and patient outcomes. Specifically, an accurate monitoring system will support the optimal clinical team necessary to achieve desired patient outcomes through improvements in communication and expedited intervention activation/therapy administration.

Because nurses' patient-related care, treatment, and management decisions directly impact patient quality of care, outcomes, and experience, it is imperative to employ an efficient clinical staff management solution capable of overcoming existing medical burdens. Through an automated staff monitoring and patient acuity tracking solution, better health outcomes (through better-focused resource allocation and more timely intervention activation and therapy administration), improved overall patient experience (through enhanced understanding of patient acuity and improved communication), and cost containment (through better, more efficient utilization) may be realized.

Use Case 4—Oncology

Cancer patients' care is impacted by extrinsic and intrinsic factors. One recent national concern around providing effective care for oncology patients is that patient preferences are not adequately communicated in a timely manner. Understanding patient preferences and improving communication are important to promote opportunities for shared decision-making that would lead to better patient care. In some disease areas such as oncology, patient preferences and feedback are extremely important due to the aggressive nature of many therapies and the adverse side effects associated with these treatments.

In this example, the patient has a scheduled elective mastectomy in 6 days. Challenges associated with this procedure include lack of patient and family understanding about the procedure itself, as well as post-op best care practices aimed at promoting the individual recovery process.

Prior to hospital admission, the patient is able to log in and access an app that allows her to identify, for example, 1) preferred rounding time, 2) preferred family notification pathway, 3) privacy preferences for communication, and 4) online health history. Upon arrival at the hospital, the patient is checked in and biometric devices (e.g., fingerprint scanner, retina scanner, etc.) may be used to confirm her identity. The patient is given a bracelet with a RFID tag that will allow her location to be tracked throughout the hospital.

The patient is admitted to the hospital for elective mastectomy for breast cancer. Upon arrival to her floor, the nurse welcomes her and reviews her pre-populated answers to the nursing assessment. The nurse confirms the answers. The patient settles in comfortably in her room and she is able to view a monitor in her room that has been programmed to display more detailed information about her diagnosis and treatment plan. The next morning, this patient is prepped for surgery and wheeled to the operating room. Her family waits is in the waiting room but is able to track the patient's progress (e.g., anesthesia, first incision, closing) from an app on their mobile devices. Only those individuals that have been explicitly given permission by the patient can access this information. The patient's family may also review frequently asked questions (FAQs) regarding her recovery process on the app. The surgery is successful, and the patient is returned to her inpatient hospital room after the effects of anesthesia are eliminated. The patient's vitals are continually monitored. The next morning, the patient's care team comes to the room at the rounding time specified by her in advance of surgery. The doctor checks her surgery wounds, monitors her vitals, and talks to her about the surgery, her condition, and her recovery. The doctor also informs her that all of the details of her individual care plan, and background on her diagnosis can be viewed on the in-room monitor for perusal at her leisure.

As the patient's care post-mastectomy progresses to her adjuvant therapy for breast cancer, educational materials tailored for her primary language, health literacy level, and treatment may be offered, during pre-visit check-in and treatment visits. Such content may be tailored to be more patient-focused in order to allow for more engaged care. Potential topics may discuss improving present symptom control and risks related to chemotherapy or offer a future context for the discussion of palliative care and end of life decision-making as a relevant concern, even at the outset of curative intent treatment.

Oncology is an area of medicine where incorporation of patient preferences can have a significant and positive impact on clinical outcomes. As a result of the complexity of decision-making throughout the oncology patient's care continuum due to the 1) existence of multiple treatment options, 2) the lack of clinical evidence or inapplicability of clinical evidence (due to evidence related to very different populations), or 3) presence of cultural beliefs that may impact treatment decisions, innovative solutions should be focused on achieving a better patient experience through a coordinated approach including both the patient and his/her treatment team.

Specifically, This solution promotes improved methods of communication and increase opportunities for patient/family awareness and engagement. For example, post-discharge status remains an area where more active and up-to-date patient monitoring mechanisms are required. Through a mobile app that administers surveys, patients can take a more participatory role in the communication of their health status and preferences to the healthcare providers. This information can help providers develop and deploy more personalized care plans targeting specific patient-voiced needs without patients having to physically visit the hospital or clinic for care.

Moreover, this innovative solution is focused on promoting patient education around various areas of this disease area to better assist patients/families understand the benefits and consequences associated with sometimes extremely aggressive and harsh therapies in order to make the best decision for that particular patient. Specifically, patient knowledge around palliative care options is important because the institution of palliative care interventions in the early stages of cancer may allow oncologists (with proper patient input and feedback) to re-align their focus on simultaneously addressing treatment concerns, as well as prominent and widespread issues like poor quality of life, or adverse symptoms or psychological distress associated with chemotherapy, radiation therapy, or other anti-cancer treatments.

As patient and family engagement becomes prioritized throughout the care process, as demonstrated by the emphasis placed on patient/family feedback by nationally recognized quality-focused organizations, such as the National Committee for Quality Assurance (NCQA) through their Patient-Centered Medical Home (PCMH) accreditation criteria, the functionality described herein will be imperative to incorporate patient/family feedback to ensure satisfaction and positive patient experience around areas of care such as access, communication, coordination, and individual care/self-management support.

Patient educational materials facilitated and presented by this functionality help to diminish the common issue of patient-physician information asymmetry. Adequate patient education is necessary to ensure patients understand, retain, and are able to put into practice the treatment plans physicians prescribe. Additionally, as quality of life and patient experience become equally prioritized in care plans, alongside more conventional treatments, (especially in areas such as oncology where palliative care consultations have consistently demonstrated statistically significant improvements in patients' symptom control, which may and oftentimes do lead to better short- and long-term outcomes for those impacted by cancer) it will be imperative that patient education focus on the benefits and costs of both curative and palliative therapies designed to both eliminate disease and reduce adverse consequences of that disease.

Use Case 5—Predictive Model

Poorly coordinated transitions of care may contribute to adverse outcomes and added substantial avoidable costs to the U.S. health care system. For example, poorly planned care transitions have amounted to unplanned readmission costs to Medicare of more than $17 billion per year. The reliable predictive model described herein is a very useful tool to predict patient utilization patterns based on where patients are going (i.e., emergency department, urgent care clinic, specialty clinic, etc.), the frequency of use of specific settings, and utilization of services in each setting, as well as specific patient complaints. Accurate patient utilization patterns will help providers tailor the patient's clinical assessment and care coordination plan around relevant patient-specific factors that may likely facilitate the efficient utilization of certain health care services and drive down unnecessary costs.

In this example, a patient has a wide array of medical and social issues. He is homeless, requires regular dialysis treatments, and suffers from schizophrenia and Crohn's disease. The patient has frequented his local hospital emergency department approximately 15 times over the last 2 months for dialysis treatments and complications related to his Crohn's disease. Additionally, he regularly visits a Dallas social service organization for his meals, shelter, and clothing. This organization also provides this patient with the mental health services he requires but is unable to afford. Upon arrival at the hospital for his dialysis treatment, the patient is given a bracelet equipped with RFID technology that allows his location to be tracked as he visits various settings of care, both clinical and social in nature. The staff explains the purpose of wearing the bracelet and seeks the patient's consent for close monitoring.

Over the course of the next month, data from the patient's RFID bracelet are provided to a predictive model that makes predictions of his future clinical and social service utilization based on 1) where he has been going (i.e., emergency department, urgent care clinic, specialty clinic, etc.), 2) the frequency of use of these specific settings, 3) utilization of services in each setting, and 4) complaints. The prediction is electronically communicated to a physician at the hospital who administers the patient's dialysis treatments. The physician may modify the patient's care plan as a result of the data he has received, and tailors future care around the prominent areas observed by the patient's past utilization patterns.

RFID technology provides useful information that allows the predictive model to forecast, with consistent and reliable accuracy, future clinical and social service utilization. This ability allows the care teams to improve care transition plans that focus on actual patient needs. Additionally, real-time visibility around patient utilization may provide opportunities for clinical organizations to interact with relevant social service organizations in an effort to improve long-term patient outcomes and health. For example, the indigent comprises a large proportion of the U.S. healthcare system's high-utilizer population, and understanding the social and clinical services these patients use enables providers to develop patient-specific care plans that have a high potential to both reduce adverse outcomes and improve the quality of life for this vulnerable population.

By focusing on coordinating care across a patient's care continuum, providers can develop care plans that better anticipate the patient's needs, and address existing patient concerns across a broad spectrum of issues, such as condition management, quality of life and functional status, and psychosocial needs. Further, an evidence-based care plan can facilitate shared-decision making, shared accountability, and the collaboration between clinical and social service organizations and the entire healthcare system at large to improve the quality of patient care and overall patient experience. It is estimated that effective care coordination may result in annual healthcare cost savings as high as 240 billion dollars.

The current system and method are operable to display, transmit, and otherwise present the list of high risk patients to the intervention coordination team, which may include physicians, physician assistants, case managers, patient navigators, nurses, social workers, family members, and other personnel or individuals involved with the patient's care. The means of presentment may include e-mail, text messages, multimedia messages, voice messages, web pages, facsimile, audible or visual alerts, etc. delivered by a number of suitable electronic or portable computing devices. The intervention coordination team may then prioritize intervention for the highest risk patients and provide targeted inpatient care and treatment. The system and method may further automatically present a care plan to include recommended intervention and treatment options. Some intervention plans may include detailed inpatient clinical assessment as well as patient nutrition, pharmacy, case manager, and heart failure education consults starting early in the patient's hospital stay. The intervention coordination team may immediately conduct the ordered inpatient clinical and social interventions. Additionally, the plan may include clinical and social outpatient interventions and developing a post-discharge plan of care and support.

High-risk patients are also assigned a set of high-intensity outpatient interventions. Once a targeted patient is discharged, outpatient intervention and care begin. Such interventions may include a follow-up phone call within 48 hours from the patient's case manager, such as a nurse; doctors' appointment reminders and medication updates; outpatient case management for 30 days; a follow-up appointment in a clinic within 7 days of discharge; a subsequent cardiology appointment if needed; and a follow-up primary care visit. Interventions that have been found to be successful are based on well-known readmission reduction programs and strategies designed to significantly reduce 30-day readmissions associated with congestive heart failure.

The clinical predictive and monitoring system and method continue to receive clinical and non-clinical data regarding the patient identified as high risk during the hospital stay and after the patient's discharge from the hospital to further improve the diagnosis and modify or augment the treatment and intervention plan, if necessary.

After the patient is discharged from the hospital, the system and method continue to monitor patient intervention status according to the electronic medical records, case management systems, social services entities, and other data sources as described above. The system and method may also interact directly with caregivers, case managers, and patients to obtain additional information and to prompt action. For example, the system and method may notify a physician that one of his or her patients has returned to the hospital, the physician can then send a pre-formatted message to the system directing it to notify a specific case management team. In another example, the clinical predictive and monitoring subsystem and method 40 may recognize that a patient missed a doctor's appointment and hasn't rescheduled. The system may send the patient a text message reminding the patient to reschedule the appointment.

Use Case 6—Situation Analysis Simulator

Clinical staffing shortages and resource limitations may have contributed to the suboptimal operating efficiency observed in many U.S. hospitals and clinics. While simulation models have been known to help clinics achieve improvements in operating efficiency by identifying the required changes necessary to improve patient experience and meet future, anticipated demand, conventional simulations may not be as reliable due to the incorporation of retrospective data that does not take into account real-time information.

For example, Clinic X has experienced a dramatic increase in the number of visiting patients over the last week. This clinic normally accepts both walk-in patients and patients with appointments. Current patient flow is approximately 80% appointments and 20% walk-ins. Due to the increase in patients coming to the clinic (both those with appointments and those walking-in), the facility has faced issues such as excessive wait times, inadequate provider capacity to provide high-quality service to patients, and a greater than expected percentage of its patients frequenting the emergency room than other comparable clinics due to poor or improper care. Additionally, once patients are waiting in examination rooms to be seen by providers, insufficient equipment and supplies further extended patient wait times.

The clinic administrator may run the situation analysis simulator to understand, given real-time data, the best mix of staff, exam rooms, clinic hours, equipment, and the optimal service time required for patients to maximize operational efficiency. Upon completion of a full simulation using real-time clinic data, the simulation function determines that clinic hours should be modified from 8 am-5 pm, Monday-Friday to 10 am-7 pm, Monday-Friday and additional hours should be added from 10 am-3 pm on Saturdays to respond to higher patient demands and achieve optimal operating efficiency. The simulation function further determines that upward adjustment of the number of examination rooms would not substantially reduce the wait time, considering other variable simulation parameters. The simulation function further determines the optimal clinical staff mix and makes a recommendation of the number of physicians, nurse practitioners, registered nurses, and technicians during office hours. The recommendation may further recommend a staggered staffing schedule so that more staff are available during the peak hours. In addition, the simulation function may recommend adding specific types of equipment based on existing and anticipated demand to minimize wait times and move patients through the examination rooms to providers more quickly.

A further clinical illustration of the functionalities of the situation analysis simulator is instructional. Many patients' poor outcomes may be attributable to hospital-specific factors such as premature discharge, rather than the patient's inability to properly manage their condition following departure from the hospital. A "red bed day" is a common term used to refer to a hospital that is above capacity and signals the need to free beds for incoming patients who may be more critical in nature. As such, hospitals are at risk of discharging patients prematurely without a complete understanding of the impact of their decision on future patient outcomes. For some patients, early discharge may not translate to any adverse event, whereas for other patients, premature discharge may equate to potentially avoidable adverse outcomes, such as readmissions or other preventable conditions.

In another example, an hospital is experiencing a "red bed day" where the hospital is at peak capacity. The clinical staff is alerted of this unfavorable status and instructed to prioritize existing patient discharges to free up beds for more critical incoming patients. A particular patient, 68 year-old black male, was admitted two days ago with a diagnosis of congestive heart failure (CHF). This patient is a recipient of Medicare, smokes regularly, and has stable familial support. Additionally, this patient has been previously identified to have hypertension and diabetes. Another patient is a 55 year-old white male who was also admitted two days ago with a diagnosis of acute myocardial infarction (AMI) and atrial fibrillation. Additionally, the second patient is identified as a recipient of Medicaid, has a history of drug abuse, and self-reports that he does not have a permanent address or stable family support. Because the need to discharge individuals to make room available for more severe patients has escalated in urgency due to the hospital's red bed status, the situation analysis simulator is used to analyze current data and generate recommendations. The situation analysis simulator is configured to provide real-time identification of patients who are at risk for an adverse event due to a specific clinical decision, such as premature discharge. Once the appropriate parameters are included in the simulator, the tool is capable of generating and presenting a risk score for both patients.

The situation analysis simulator identifies the first patient as someone with a low-risk for readmission. Therefore, the system identifies the first patient for immediate discharge. The first patient is thus discharged with appropriate discharge instructions by the case manager on shift, including information for a scheduled follow-up appointment and phone call. The situation analysis simulator further identifies the second patient as high-risk for readmission. Accordingly, despite the dire "red bed" status, the second patient stays in the hospital and continues to receive the on-site care he needs to improve his condition.

The situation analysis simulator is a tool capable of simulating 'What-If' scenarios by analyzing the impact of discharging individual patients during high volume days will facilitate effective discharge planning in order to reduce the likelihood of future poor patient clinical outcomes. The use of real-time data to run the simulations provides reasonable confidence in the application of simulated results to current and future clinical planning (such as around discharge prioritization). Furthermore, while other existing solutions are capable of running a simulation, the novel feature described herein is the ability to simulate data over a shorter, more recent period allowing the hospital to behave proactively to prevent likely adverse patient events rather than reacting to an adverse outcome that has occurred, but that could have been prevented.

As a result of identifying barriers to effective care through the use of real-time data incorporated into the situation analysis simulator tool, the hospital is able to improve population health and the overall patient experience by immediately prioritizing more vulnerable patients during periods of resource shortages. Specifically with regard to discharge planning, hospitals can, reliably and with greater confidence and speed, deliver more focused care for individuals at increased risk of adverse outcomes (such as a re-hospitalization), as identified by the Situation Analysis Simulator despite hospital-specific factors, such as red bed days.

The system and method as described herein are operable to harness, simplify, sort, and present patient information in real-time or near real-time, predict and identify highest risk patients, identify adverse events, coordinate and alert practitioners, and monitor patient outcomes across time and space. The present system improves healthcare efficiency, assists with resource allocation, and presents the crucial information that lead to better patient outcomes.

The features of the present invention which are believed to be novel are set forth below with particularity in the appended claims. However, modifications, variations, and changes to the exemplary embodiments described above will be apparent to those skilled in the art, and the system and method described herein thus encompasses such modifications, variations, and changes and are not limited to the specific embodiments described herein.

What is claimed is:

1. A holistic hospital patient care and management system comprising:
   a data store operable to receive and store data associated with a plurality of patients including clinical and non-clinical data, the clinical data are selected from at least one member of the group consisting of: vital signs and other physiological data; data associated with physical exams by a physician, nurse, or allied health professional; medical history; allergy and adverse medical reactions; family medical information; prior surgical information; emergency room records; medication administration records; culture results; dictated clinical notes and records; gynecological and obstetric information; mental status examination; vaccination records; radiological imaging exams; invasive visualization procedures; psychiatric treatment information; prior histological specimens; laboratory data; genetic information; physician's and nurses' notes; networked devices and monitors; pharmaceutical and supplement intake information; and focused genotype testing; and the non-clinical data are selected from at least one member of the group consisting of: social, behavioral, lifestyle, and economic data; type and nature of employment data; job history data; medical insurance information; hospital utilization patterns; exercise information; addictive substance use data; occupational chemical exposure records; frequency of physician or health system contact logs; location and frequency of habitation change data; predictive screening health questionnaires; personality tests; census and demographic data; neighborhood environment data; dietary data; participation in food, housing, and utilities assistance registries; gender; marital status; education data; proximity and number of family or care-giving assistant data; address data; housing status data; social media data; educational level data; and data entered by patients;
   a plurality of RFID sensors configured to detect a plurality of RFID tags associated with the plurality of patients to enable real-time tracking of location and status;
   at least one predictive model including a plurality of weighted risk variables and risk thresholds in consideration of the clinical and non-clinical data and configured to identify at least one medical condition associated with the plurality of patients;
   a risk logic module configured to apply the at least one predictive model to the clinical and non-clinical data to determine at least one risk score associated with each of the plurality of patients, and to stratify the risks associated with the plurality of patients in response to the risk scores;
   a patient monitoring logic module configured to receive location data associated with the plurality of patients from the RFID sensors, and analyze and record patient real-time location and status; and
   a user interface module configured to inquire and receive location monitoring permission from the plurality of patients on a specified device, and display patient medical condition, risk score, location, and status information to authorized personnel on the specified device.

2. The system of claim 1, wherein the plurality of RFID sensors are distributed inside a medical facility.

3. The system of claim 1, wherein the plurality of RFID sensors are distributed inside a social service facility.

4. The system of claim 1, wherein the risk logic module further comprises a disease identification logic module configured to analyze the clinical and non-clinical data associated with a patient and identify the at least one medical condition associated with the patient.

5. The system of claim 1, wherein the risk logic module further comprises a natural language processing and generation logic module configured to process and analyze clinical and non-clinical data expressed in natural language, and to generate an output expressed in natural language.

6. The system of claim 1, wherein the risk logic module further comprises an artificial intelligence logic module configured to detect, analyze, and verify trends indicated in the clinical and non-clinical data and modify the plurality of weighted risk variables and risk thresholds in response to detected and verified trends indicated in the clinical and non-clinical data.

7. The system of claim 1, wherein the user interface module is configured to display a list of the plurality of patients, and status and location of each patient, including attendance to scheduled appointments.

8. The system of claim 1, wherein the patient monitoring logic module is configured to determine the status of a patient in response to the detected location of the patient.

9. A holistic hospital patient care and management system, comprising:
   a repository of patient data including clinical and non-clinical data associated with a plurality of patients updated and received from a plurality of clinical and social service organizations and data sources;
   a plurality of presence detection sensors distributed inside the plurality of clinical and social service organizations and configured to detect a plurality of tags associated with a plurality of patients to enable real-time tracking of location and status;

at least one predictive model using clinical and social factors derived from the patient data to extract both explicitly encoded information and implicit information about the patient's clinical and non-clinical data to identify at least one patient having at least one medical condition requiring medical care;

a risk logic module configured to apply the at least one predictive model to the clinical and non-clinical data, including the location and status of the at least one patient, to determine at least one risk score associated with the at least one patient, and to stratify the patient's risk associated with the at least one patient related to the at least one medical condition in response to the risk score;

a patient monitoring logic module configured to receive location data from the presence detection sensors, and analyze patient real-time location and status; and a data presentation module configured to query and receive location monitoring permission from the at least one patient, and display patient location and status information on a specified device.

10. The system of claim 9, wherein the specified device is selected from the group consisting of a mobile telephone, a laptop, a desktop computer, and a display monitor.

11. The system of claim 9, wherein the risk logic module further comprises a disease identification logic module configured to analyze the clinical and non-clinical data, including patient location and status, associated with a particular patient and identify the at least one medical condition associated with the patient.

12. The system of claim 9, wherein the risk logic module further comprises a natural language processing and generation logic module configured to process and analyze clinical and non-clinical data expressed in natural language, and to generate an output expressed in natural language.

13. The system of claim 9, wherein the risk logic module further comprises an artificial intelligence logic module configured to detect, analyze, and verify trends indicated in the clinical and non-clinical data and modify the plurality of weighted risk variables and risk thresholds in response to detected and verified trends indicated in the clinical and non-clinical data.

14. The system of claim 9, wherein the data presentation module is configured to display a list of patients, and location and status of each patient.

15. The system of claim 9, wherein the patient monitoring logic module is configured to automatically determine the status of a patient in response to the detected location of the patient.

16. A holistic hospital patient care and management method, comprising:

receiving real-time patient data including clinical and non-clinical data associated with a plurality of patients admitted to a hospital;

applying at least one predictive model using clinical and social factors derived from the patient data to extract and translate both structured and unstructured information and implicit information about the patient's clinical and non-clinical data to identify at least one patient having at least one medical condition requiring medical care;

receiving real-time location data from a plurality of RFID sensors configured to detect a plurality of RFID tags associated with the plurality of patients;

analyzing patient real-time location data and determining patient status; and presenting patient location and status information on a specified device.

17. The method of claim 16, wherein presenting patient location and status information comprises using a specified device selected from the group consisting of a mobile telephone, a laptop, a desktop computer, and a display monitor.

18. The method of claim 16, further comprising analyzing the clinical and non-clinical data associated with a particular patient and identifying the at least one medical condition associated with the patient.

19. The method of claim 16, further comprising processing and analyzing clinical and non-clinical data expressed in natural language, and to generate an output expressed in natural language.

20. The method of claim 16, comprising detecting, analyzing, and verifying trends indicated in the clinical and non-clinical data and modifying a plurality of weighted risk variables and risk thresholds used in the predictive model in response to detected and verified trends indicated in the clinical and non-clinical data.

* * * * *